United States Patent [19]

Ishio et al.

[11] Patent Number: 5,547,791
[45] Date of Patent: Aug. 20, 1996

[54] ELECTROPHOTOGRAPHIC PHOTORECEPTOR

[75] Inventors: Kozo Ishio; Tetsuo Murayama, both of Machida, Japan

[73] Assignee: Mitsubishi Chemical Corporation, Tokyo, Japan

[21] Appl. No.: 347,132

[22] Filed: Nov. 23, 1994

[30] Foreign Application Priority Data

Nov. 26, 1993 [JP] Japan .................................. 5-296778
Jun. 3, 1994 [JP] Japan .................................. 6-122651

[51] Int. Cl.$^6$ ...................................................... G03G 5/04
[52] U.S. Cl. ................................................ 430/59; 430/76
[58] Field of Search .................................. 430/59, 73, 76

[56] References Cited

U.S. PATENT DOCUMENTS 4,403,025  9/1983  Horie et al. ............................... 430/59
4,987,045  1/1991  Suzuki et al. ............................. 430/59
5,284,728  2/1994  Murayama et al. ...................... 430/59

FOREIGN PATENT DOCUMENTS 0144791   6/1985   European Pat. Off. .
0226751   7/1987   European Pat. Off. .
3124396   7/1982   Germany .
3813459  11/1988   Germany .

*Primary Examiner*—John Goodrow
*Attorney, Agent, or Firm*—Oblon, Spivak, McClelland, Maier & Neustadt, P.C.

[57] ABSTRACT

An electrophotographic photoreceptor of the present invention comprises on a conductive support a photosensitive layer containing an arylamine hydrazone compound which has —O—A substituent on aryl moiety. The electrophotographic photoreceptor of the present invention exhibits a very high sensitivity and a lowering in residual potential. It is excellent in durability.

11 Claims, 5 Drawing Sheets

ELECTROPHOTOGRAPHIC PHOTORECEPTOR

FIELD OF THE INVENTION

The present invention relates to an electrophotographic photoreceptor. More specifically, it relates to a high sensitive electrophotographic photoreceptor having a photosensitive layer which contains an organic photoconductive material.

PRIOR ART

In the previously known electrophotographic photoreceptors, photosensitive layers have generally been formed from inorganic photoconductive materials such as selenium, cadmium sulfide, zinc oxide and the like. These conventional materials, however, are not completely free from drawbacks. Precisely, selenium and cadmium sulfide are required to be recovered because they are toxic, selenium is poor in heat resistance because it is liable to crystallize on heating, cadmiun sulfide and zinc oxide are poor in moisture resistance, while zinc oxide is poor in printing resistance. This is the reason why considerable efforts have been continued to develop novel electrophotographic photoreceptors. Researches on organic photoconductive materials suitable for use in photosensitive layers of an electrophotographic photoreceptor have recently been progressed, and some of such materials have been put to practical use. Organic photoconductive materials, as compared to inorganic materials, are advantageous in that they are of lighter weight, more adaptable to film formation, more easily to be processed into photoreceptor, able to form a transparent photoreceptor depending on their nature and so on.

Presently much attention has been directed towards the development of so-called double-layed photoconductive structures in which carrier generate layers are fromed from one compound and carrier transport layers are formed from another compound, since these structures are considered effective in sensitivity improvement. In fact, these structures containing organic compounds are also put to practical use.

Carrier transport medium (hereinafter abbreviated as "CTM") may consist of a high molecular photoconductive compound such as polyvinyl carbazole, or a low molecular photoconductive compound dispersed or dissolved in a binder polymer.

In particular, organic low molecular photoconductive compounds would easily give the electrophotographic photoreceptor exhibiting good mechanical properties, because the binders therefor could be selected from the polymers excellent in film-forming properties, flexibility and adhesive properties (see, for example, JP-A-63172161, JP-A-63174053, JP-A-04-267261 and JP-B-93015259).

Required performances of an electrophotographic photoreceptor are mentioned as follows: (1) a high chargeability during corona discharge in the dark; (2) a small attenuation in surface voltage during corona charge in the dark; (3) a great attenuation in surface voltage during light irradiation; (4) a low residual potential after light irradiation; (5) the change of surface potential, the lowering of sensitivity and the accumulation of residual potential on repeated use are small, allowing good durability; (6) the lowerings of surface voltage and sensitivity as well as the increase of residual potential when exposed to intense light are small and able to be quickly restored.

Especially when residual potential is high, electrical charges are remained also in exposed portions. If toner development is performed, toner will be developed also in non-printing areas, resulting in so-called foggy images. Whereas if reversal development is carried out as commonly used in a printer etc., the density or contrast of printed images becomes lower, and in extreme cases, toner may fail to attach to the printing areas, resulting in so-called void images. Both may remarkably deteriorate the reproducibility of printed images, making them incapable of practical use.

On the other hand, if the lowerings in surface voltage and sensitivity as well as the increase in residual potential are great when the photoreceptors are exposed to intense light, the reproducibility of printed images is remarkabley declined. So it is desirable that the lowerings in surface voltage and sensitivity as well as the increase in residual potential are small and able to be quickly restored. Behavior of a photoreceptor when exposed to intense light is called intense exposure properties. The lowering extent of surface voltage is represented by the retention percentage at intense exposure and the extent of restoration of lowered surface voltage is represented by the restoration percentage at intense exposure. The higher values of both are more desirable.

In recent years, since laser printers adopting reversal developing system have been wide spread, there has been a growing demand for CTMs which are high in sensitivity, low in residual potential and excellent in durablility and which preferably are combined with charge generate materials for long wave length light such as phthalocyanine pigments. As laser printers are highly probable to be exposed to intense light during maintenance, good intense exposure properties are required for CTMs.

SUMMARY OF THE INVENTION

The inventors, concentrated their efforts on organic low molecular photoconductive compounds able to provide an electrophotographic photoreceptor which exhibits good intense exposure properties, a high sensitivity, a low residual potential and an excellent durability, have found that the specified arylamine hydrazone compounds are particularly advantageous and thus accomplished the present invention.

The aspect of the present invention, therefore, is to provide an electrophotographic photoreceptor comprising on a conductive support a photosensitive layer which contains an arylamine hydrazone compound represented by the general formula (I) below:

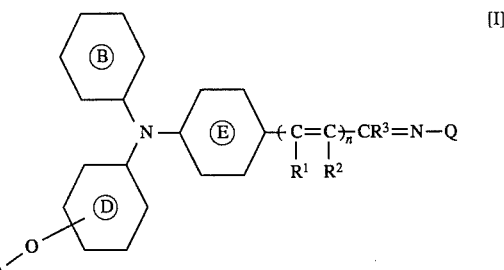

in which,
A represents a group of the general formula (II), (III) or (IV);

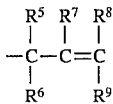

[IV]

Q represents a group of the general formula (V);

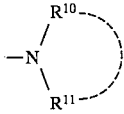

[V]

n is zero or an integer equal to or more than 1;

X represents an optionally substituted alkylene group;

Ar represents an optionally substituted aryl group or an optionally substituted heterocyclic group;

B, D and E each represents an optionally substituted benzene ring and may be identical or different each other;

$R^1$, $R^2$, $R^3$, $R^5$, $R^6$, $R^7$, $R^8$ and $R^9$ each represents a hydrogen atom, an optionally substituted alkyl group, an optionally substituted aryl group or an optionally substituted heterocyclic group, provided that when n is equal to or more than 2, each $R^1$ in each structural unit identical or different, and the same is true case of $R^2$;

$R^4$ represents an optionally substituted alkyl group, an optionally substituted aryl group, an optionally substituted heterocyclic group or an optionally substituted aralkyl group;

$R^{10}$ and $R^{11}$ each represents an optionally substituted aryl group, an optionally substituted heterocyclic group, an optionally substituted alkyl group, an optionally substituted aralkyl group or allyl group, provided that $R^{10}$ and $R^{11}$ may be bonded directly or by means of a linkng group.

BRIEF DESCRIPTION OF THE INVENTION

FIG. 1 is an infrared absorption spectrogram of the arylamine hydrazone compound of the present invention synthesized in Preparation 1, FIG. 2 is an infrared absorption spectrogram of the arylamine hydrazone compound of the present invention synthesized in Preparation 2, FIG. 3 is an infrared absorption spectrogram of the arylamine hydrazone compound of the present invention synthesized in Preparation 3, FIG. 4 is an infrared absorption spectrogram of the arylamine hydrazone compound of the present invention synthesized in Preparation 5, and FIG. 5 is an infrared absorption spectrogram of the arylamine hydrazone compound of the present invention synthesized in Preparation 6.

DETAILED DESCRIPTION OF THE INVENTION

Figure 1:
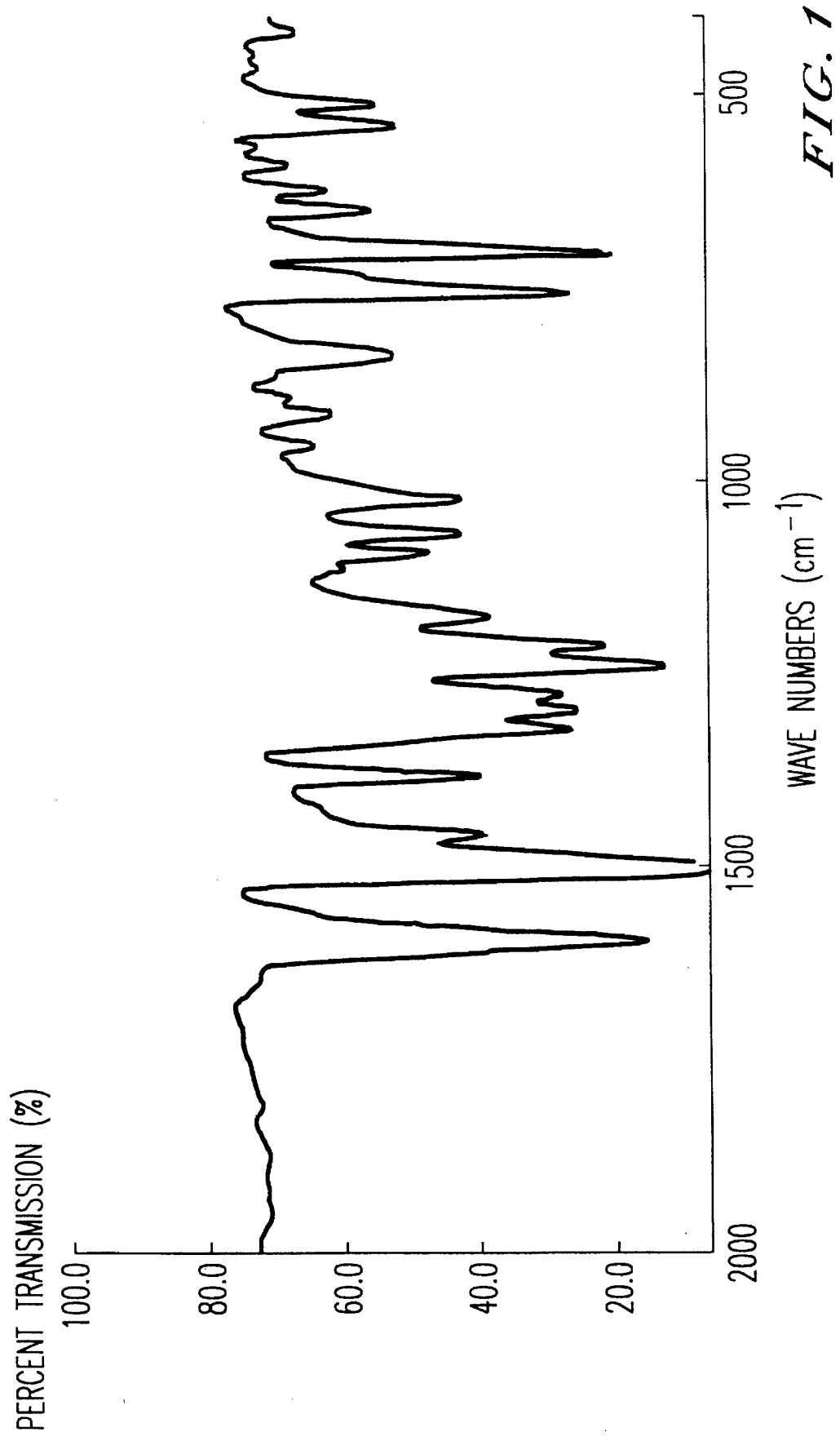

The present invention will now be described in detail.

The electrophotographic photoreceptor of the present invention contains in the photosensitive layer thereof an arylamine hydrazone compound represented by the general formula (I) above. As for this arylamine hydrazone, the skeletal structure thereof itself is known from the JP-B-85034099 and the substituents on aryl mentioned therein are a C1 to C4 alkoxy group and an aryloxy group. However, no mention is made of the substituents specified in the present invention, i.e. the substituents corresponding to a group —O—A.

According to the present invention, the substituent A in the general formula (I) represents a group corresponding to the general formula (II):

—X—Ar    [II]

the general formula (III):

[III]

or the general formula (IV):

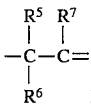

[IV]

In particular, a group of the formula (II) or (IV) is preferable and a group of the formula (IV) is more preferable.

Q represents a group corresponding to the general formula (V):

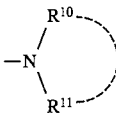

[V]

n is 0 or an integer equal to or more than 1, preferably 0 to 3, more preferabley 0 or 1.

X represents an alkylene group including methylene, ethylene and propylene groups, preferably an alkylene group having 1 to 3 carbon atoms. Methylene group is particularly preferred. These alkylene groups may be optionally substituted and the substituents which may be mentioned are lower alkyl groups such as methyl and ethyl groups; lower alkoxy groups such as methoxy and ethoxy groups; halogen atoms such as chlorine and bromine atoms; aryl groups such as phenyl and naphtyl groups.

Ar represents an aryl group such as phenyl, naphtyl or anthracenyl group; and a heterocyclic group such as pyrrolyl, thienyl, furyl or carbazolyl groups, and phenyl group is particularly preferred. These aryl groups and heterocyclic groups may be optionally substituted and the substituents which may be mentioned are halogen atoms such as chlorine, bromine and iodine atoms; alkyl groups such as methyl, ethyl, propyl, butyl and hexyl groups; alkoxy groups such as methoxy, ethoxy and butoxy groups; allyl group; aralkyl groups such as benzyl, naphtylmethyl and phenetyl groups; aryloxy groups such as phenoxy and tolyloxy groups; arylalkoxy groups such as benzyloxy and phenetyloxy groups; aryl groups such as phenyl and naphtyl groups; arylvinyl groups such as styryl and naphtylvinyl groups as well as dialkylamino groups such as dimethylamino and diethylamino groups; diarylamino groups such as diphenylamino and dinaphtylamino groups; diaralkylamino groups such as dibenzylamino and diphenetylamino groups; diheterocyclic amino groups such as dipyridylamino and dithienylamino groups; diallylamino group; and di-substituted amino groups containing a combination of substituents selected from the amino groups mentioned above.

B, D and E each represents a benzene ring optionally substituted with one or more of substituents, and the substituents which may be mentioned are halogen atoms such as chlorine, bromine and iodine atoms; alkyl groups such as methyl, ethyl and propyl groups; alkoxy groups such as methoxy, ethoxy and propyloxy groups; aryl groups such as phenyl and naphtyl groups as well as dialkylamino groups such as dimethylamino group; diarylamino groups such as diphenylamino group; diaralkylamino groups such as dibenzylamino group; diheterocyclic amino groups such as dipyridylamino group; diallylamino group; and di-substituted amino groups containing a combination of substituents selected from the amino groups mentioned above. When two or more substituents are present, they may identical or different each other. A hydrogen atom, a methyl group or a methoxy group is particularly preferred. These alkyl groups, alkoxy groups and aryl groups may be optionally substituted and the substituents which may be mentioned are a hydroxyl group; halogen atoms such as chlorine, bromine and iodine atoms; alkyl groups such as methyl, ethyl, propyl, butyl and hexyl groups; alkoxy groups such as methoxy, ethoxy and buthoxy groups; allyl group; aralkyl groups such as benzyl, naphtylmethyl and phenetyl groups; aryloxy groups such as phenoxy and tolyloxy groups; arylalkoxy groups such as benzyloxy and phenetyloxy groups; aryl groups such as phenyl and naphtyl groups; arylvinyl groups such as styryl and naphtylvinyl groups as well as dialkylamino groups such as dimethylamino and diethylamino groups; diarylamino groups such as diphenylamino and dinaphtylamino groups; diaralkylamino groups such as dibenzylamino and diphenetylamino groups; diheterocyclic amino groups such as dipyridylamino and dithienylamino groups; diallylamino group; and di-substituted amino groups containing a combination of substituents selected from the amino groups mentioned above.

$R^1$, $R^2$, $R^3$, $R^5$, $R^6$, $R^7$, $R^8$ and $R^9$ each represents a hydrogen atom; an alkyl group such as methyl, ethyl or propyl groups; an aryl group such as phenyl, naphtyl or anthracenyl groups; and a heterocyclic group such as pyrrolyl, thienyl, furyl or carbazolyl groups. These alkyl groups, aryl groups and heterocyclic groups may be optionally substituted and the substituents which may be mentioned are halogen atoms such as chlorine, bromine and iodine atoms; alkyl groups such methyl, ethyl, propyl, butyl and hexyl groups; alkoxy groups such as methoxy, ethoxy and butoxy groups; allyl group; aralkyl groups such as benzyl group, naphtylmethyl and phenetyl groups; aryloxy groups such as phenoxy and tolyloxy groups; arylalkoxy groups such as benzyloxy and phenetyloxy groups; aryl groups such as phenyl and naphtyl groups; arylvinyl groups such as styryl and naphtylvinyl group as well as dialkylamino groups such as dimethylamino and diethylamino groups; diarylamino groups such as diphenylamino and dinaphtylamino groups; diaralkylamino groups such as dibenzylamino and diphenetylamino groups; diheterocyclic amino groups such as dipyridylamino and dithienylamino groups; diallylamino group; and di-substituted amino groups containing a combination of substituents selected from the amino groups mentioned above.

When n is equal to or more than 2, $R^1$ and $R^2$ may be identical or different each other.

$R^4$ represents an alkyl group such as methyl, ethyl or propyl groups; an aryl group such as phenyl, naphtyl or anthracenyl groups; a heterocyclic group such as pyrrolyl, thienyl, furyl or carbazolyl groups; and an aralkyl group such as benzyl or phenetyl and an alkyl groups, especially an alkyl group having 1 to 3 carbon atoms is preferred. These alkyl groups, aryl groups, heterocyclic groups and aralkyl groups may be optionally substituted and the substituents which may be mentioned are halogen atoms such as chlorine, bromine and iodine atoms; alkyl groups such as methyl, ethyl, propyl, butyl and hexyl groups; alkoxy groups such as methoxy, ethoxy and butoxy groups; allyl group; aralkyl groups such as benzyl, naphtylmethyl and phenetyl groups; aryloxy groups such as phenoxy and tolyloxy groups; arylalkoxy groups such as benzyloxy and phenetyloxy groups; aryl groups such as phenyl and naphtyl groups; arylvinyl groups such as styryl and naphtylvinyl groups as well as dialkylamino groups such as dimethylamino and diethylamino groups; diarylamino groups such as diphenylamino and dinaphtylamino groups; diaralkylamino groups such as dibenzylamino and diphenetylamino groups; diheterocyclic amino groups such as dipyridylamino and dithienylamino groups; diallylamino group; and di-substituted amino groups containing a combination of substituents selected from the amino groups mentioned above.

$R^{10}$ and $R^{11}$ each represents an aryl group such as phenyl, naphtyl or anthracenyl groups; a heterocyclic group such as pyrrolyl, thienyl, furyl or carbazolyl groups; an alkyl group such as methyl, ethyl or propyl groups; an aralkyl group such as benzyl or phenetyl groups; and an allyl group. These aryl groups, heterocyclic groups, alkyl groups and aralkyl groups may be optionally substituted and the substituents which may be mentioned are halogen atoms such as chlorine, bromine and iodine atoms; alkyl groups such as methyl, ethyl, propyl, butyl and hexyl groups; alkoxy groups such as methoxy, ethoxy and butoxy groups; allyl group; aralkyl groups such as benzyl, naphtylmethyl and phenetyl groups; aryloxy groups such as phenoxy and tolyloxy groups; arylalkoxy groups such as benzyloxy and phenetyloxy groups; aryl groups such as phenyl and naphtyl groups; arylvinyl groups such as styryl and naphtylvinyl groups as well as dialkylamino groups such as dimethylamino and diethylamino groups; diarylamino groups such as diphenylamino and dinaphtylamino groups; diaralkylamino groups such as dibenzylamino and diphenetylamino groups; diheterocyclic amino groups such as dipyridyl amino and dithienyl amino groups; diallylamino group; and di-substituted amino groups containing a combination of substituents selected from the amino groups mentioned above. Preferably, at least one of $R^{10}$ and $R^{11}$ represents an optionally substituted aryl group.

Furthermore, $R^{10}$ and $R^{11}$ may be bonded directly or by means of a linking group.

Linking groups which may be mentioned are alkylene groups such as methylene, ethylene and trimethylene groups; and hetero atoms such as —S—, —O— and —N—, preferabley —S—, —O— and —CH$_2$—, more preferably —S—.

Preferable examples of Q in which $R^{10}$ and $R^{11}$ are bonded by means of a linking group are those represented by the general formulae (VI), (VII), (VIII) and (IX) below:

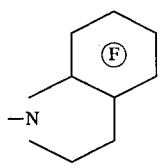

(VI)

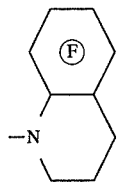

(VII)

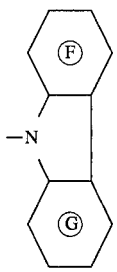
(VIII)

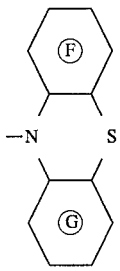
(IX)

in which F and G each represents a benzen ring which is optionally substituted with a halogen atom, an optionally substituted alkyl group, an optionally substituted alkoxy group, an optionally substituted aryl or a substituted amino group, and F and G may be identical or different each other.

Typical examples of arylamine hydrazone compounds of the general formula (I) are set forth in the following. These compounds are illustrated only by way of examples without limiting the scope of arylamine hydrazone compounds to be used in the present invention.

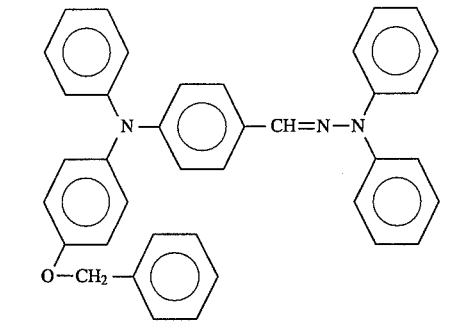
1

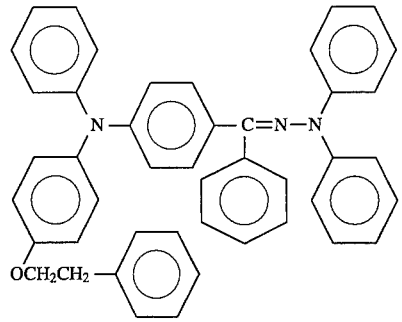
2

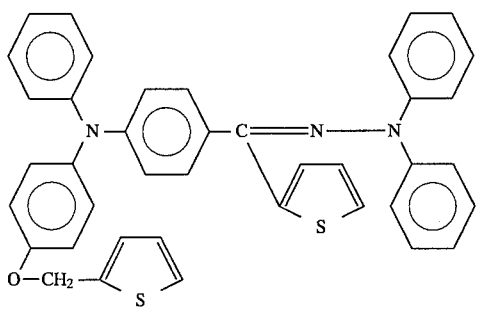
3

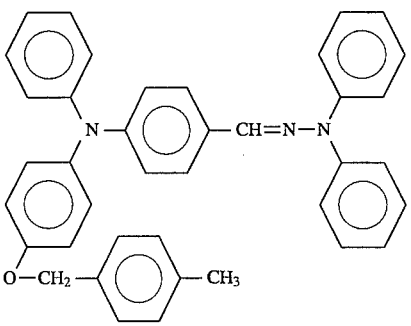
4

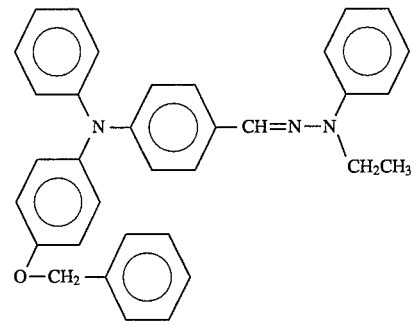
5

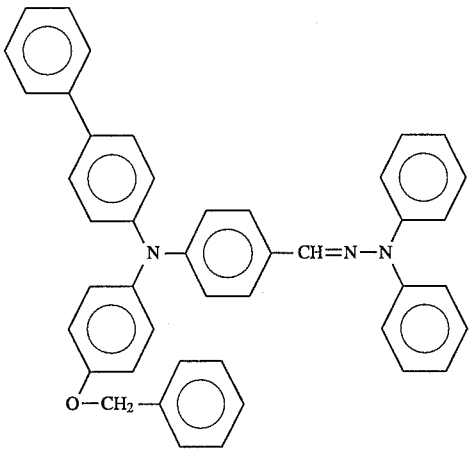
6

-continued
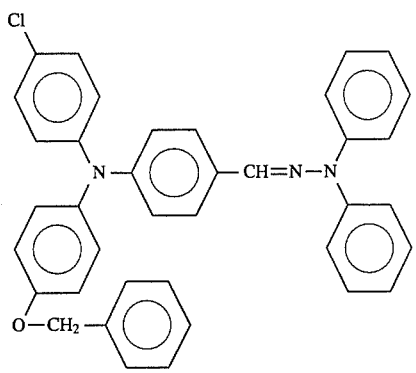
7
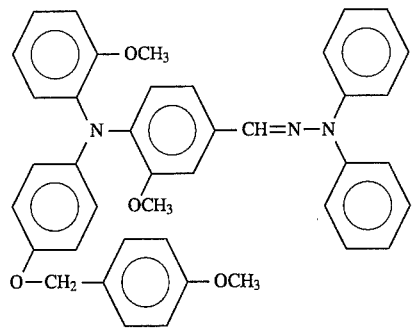
8
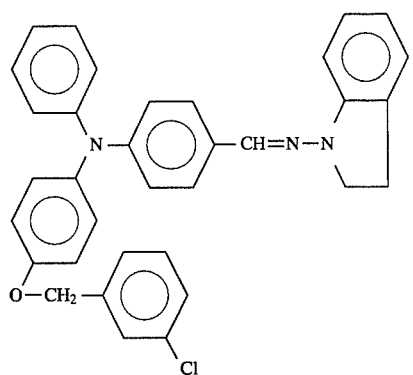
9
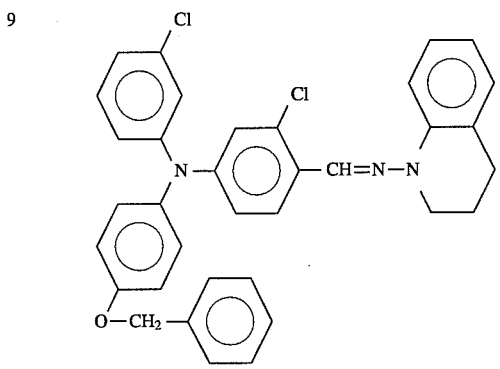
10
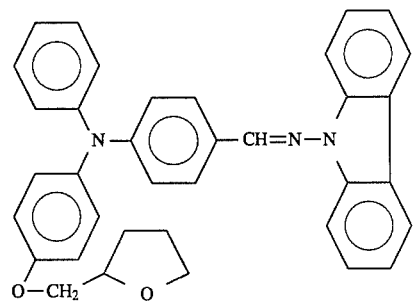
11
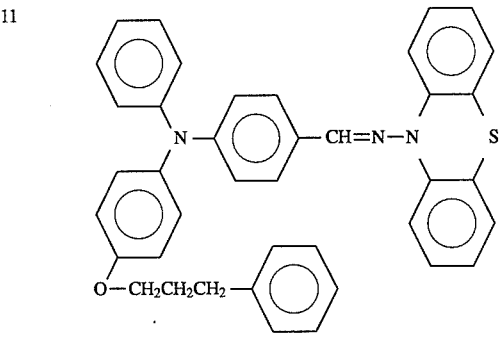
12
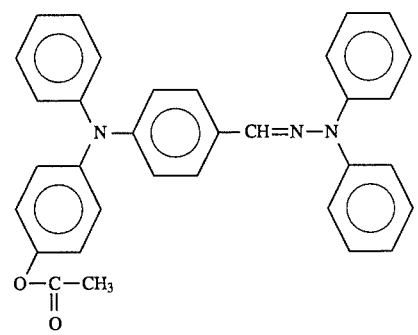
13
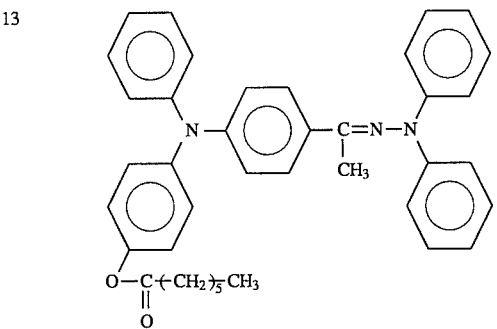
14

-continued
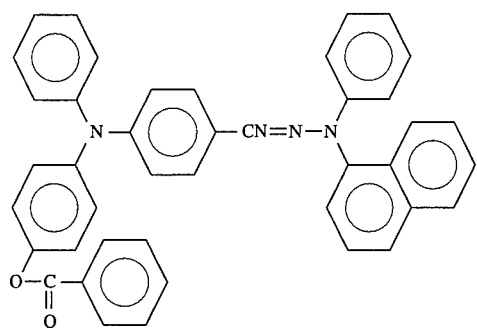
15
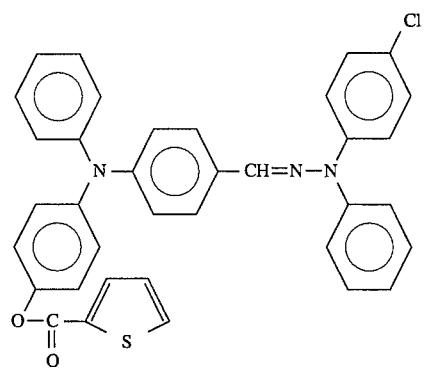
16
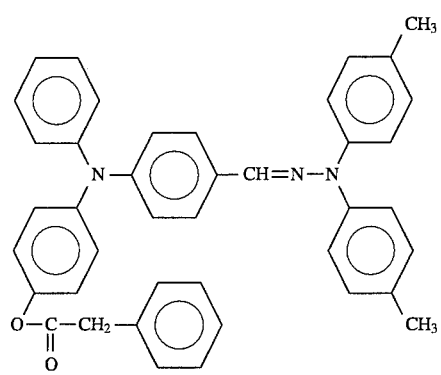
17
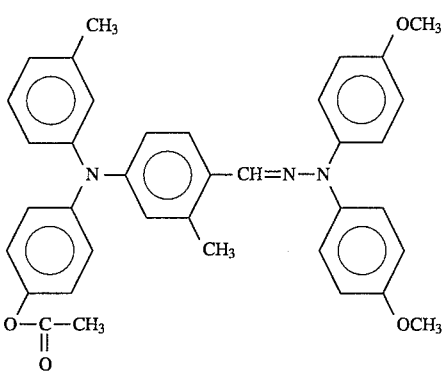
18
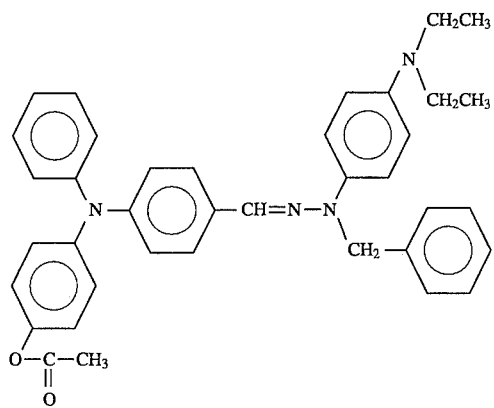
19
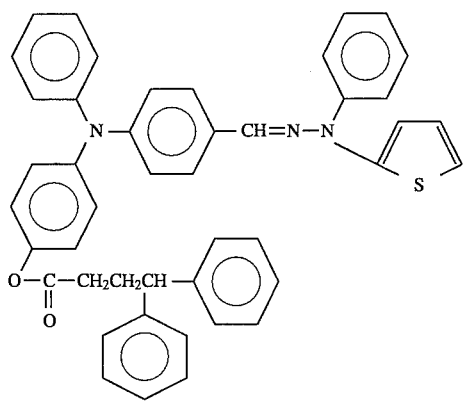
20
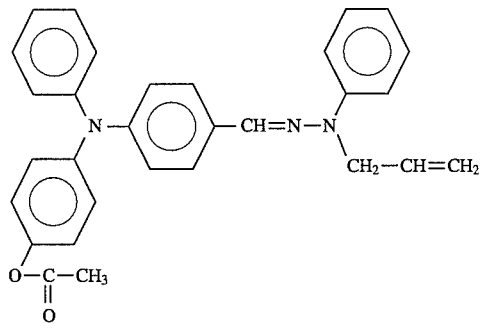
21
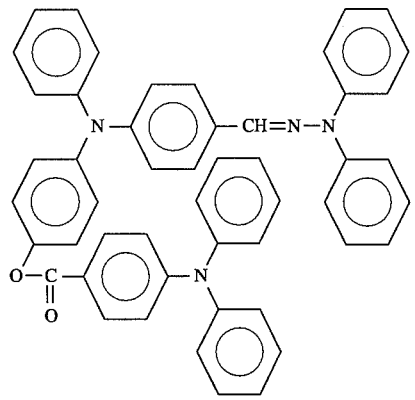
22

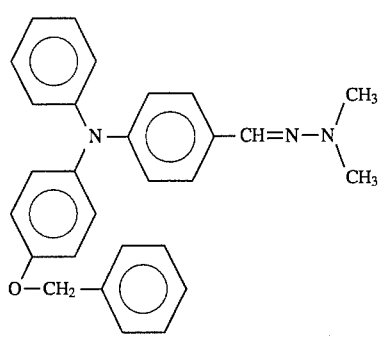
23
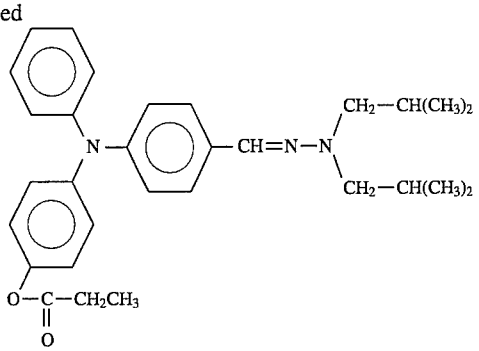
24
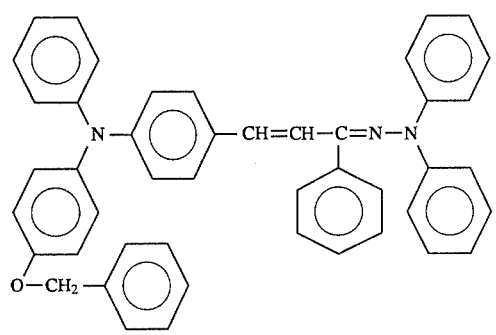
25
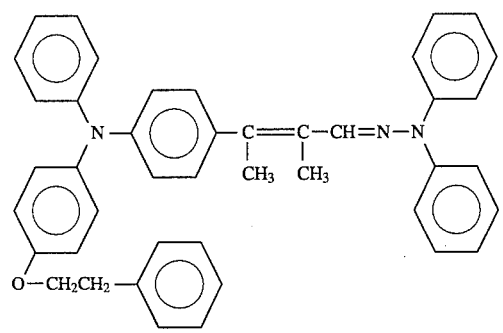
26
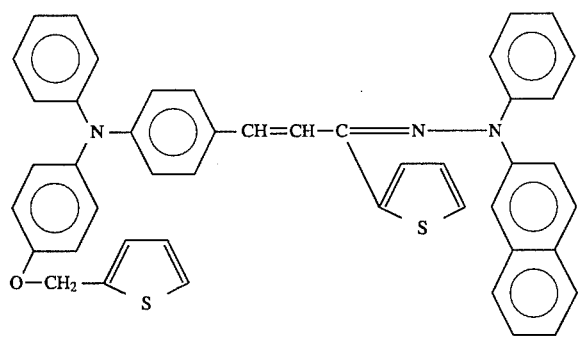
27
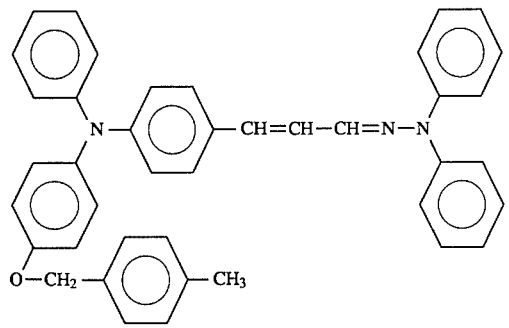
28
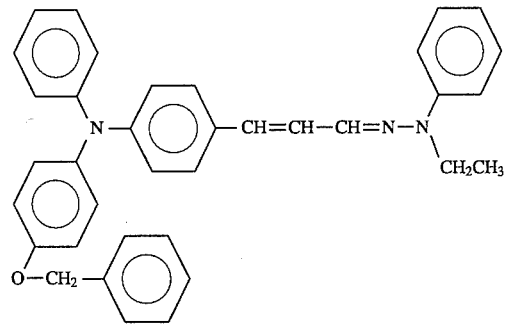
29

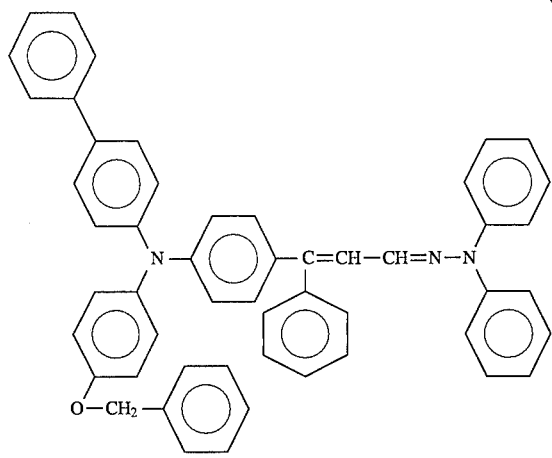
30
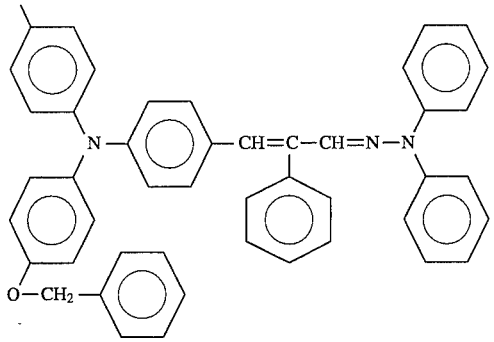
31
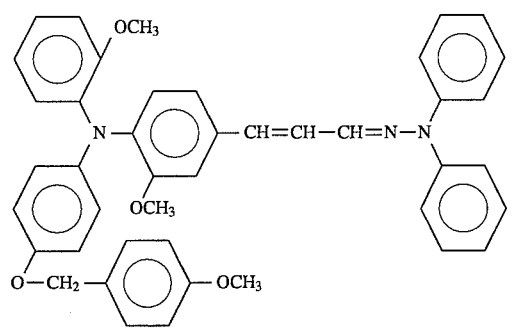
32
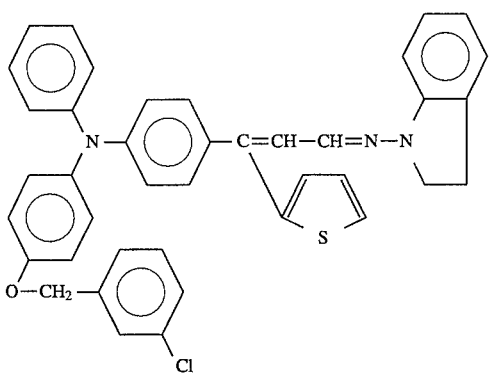
33
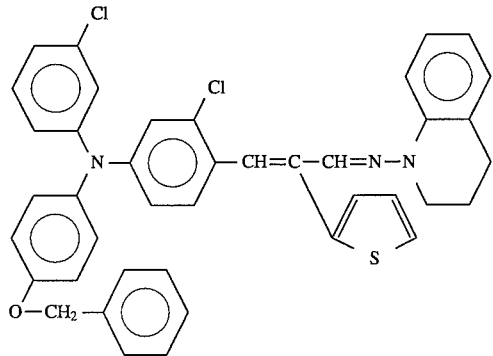
34
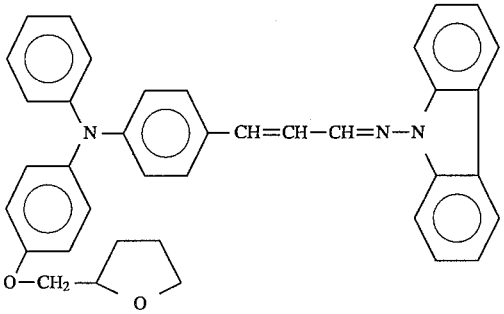
35
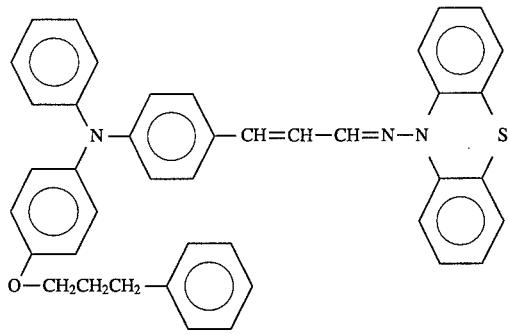
36

37
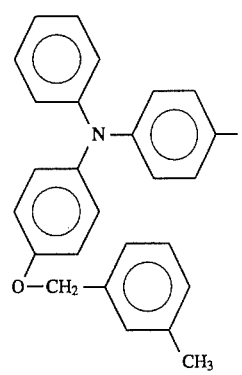
38
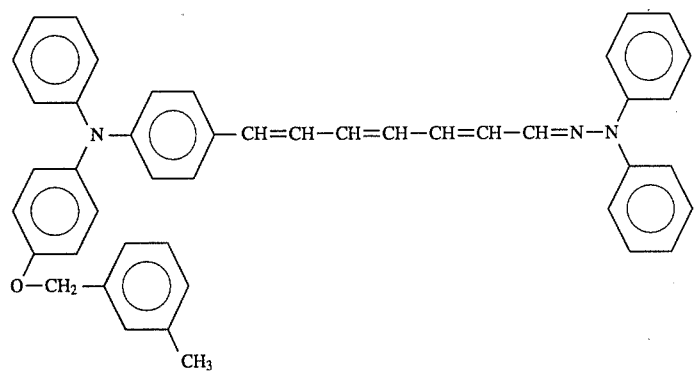
39
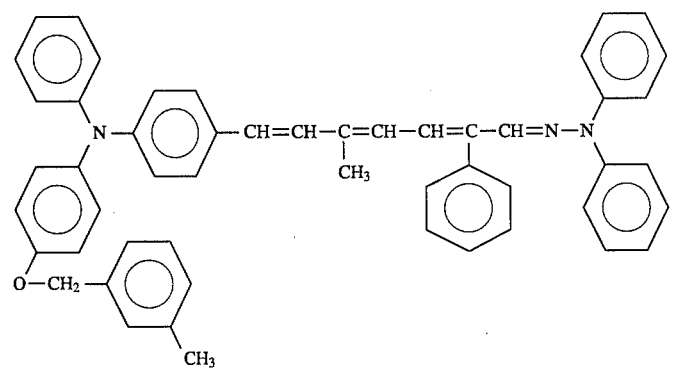
40
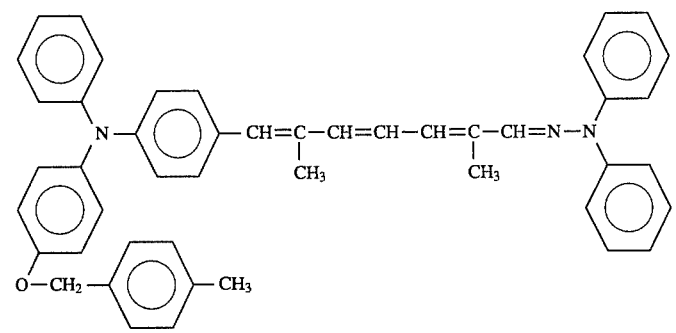

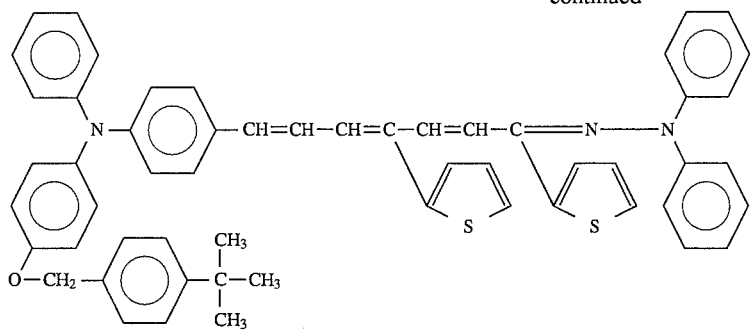
41
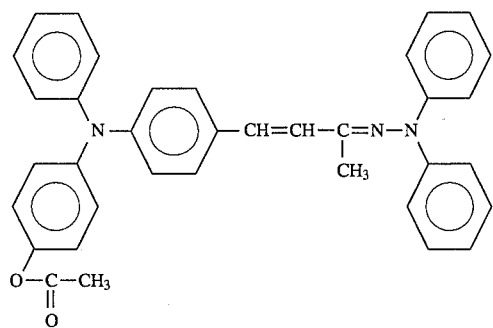
42
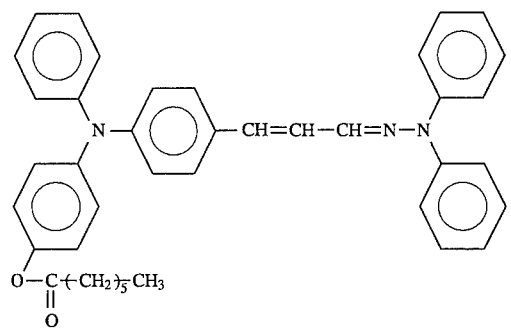
43
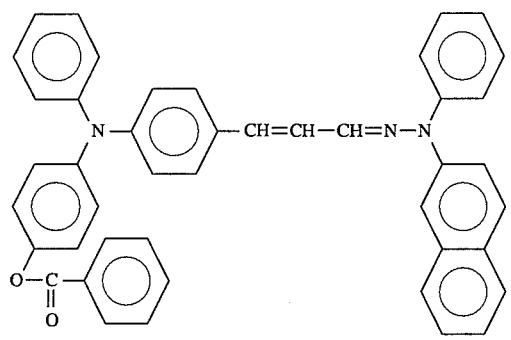
44
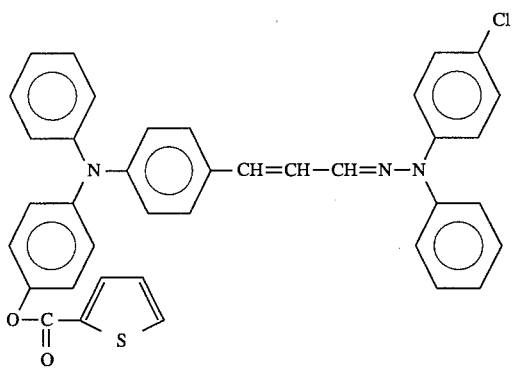
45
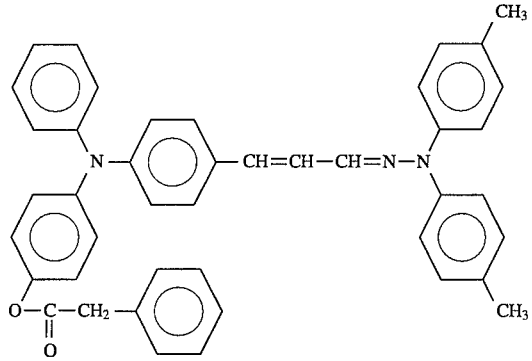
46
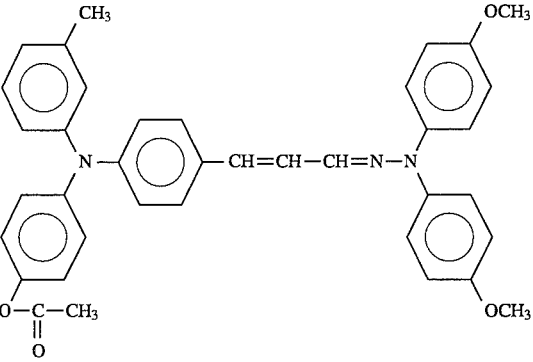
47

-continued
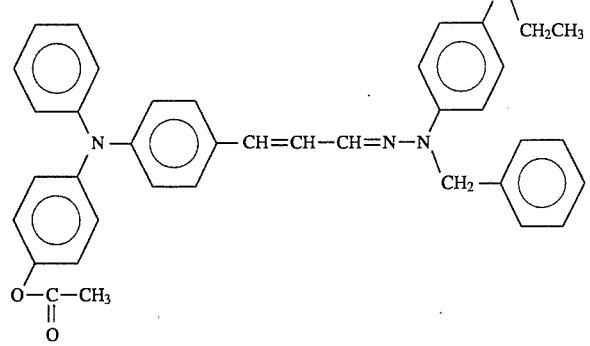
48
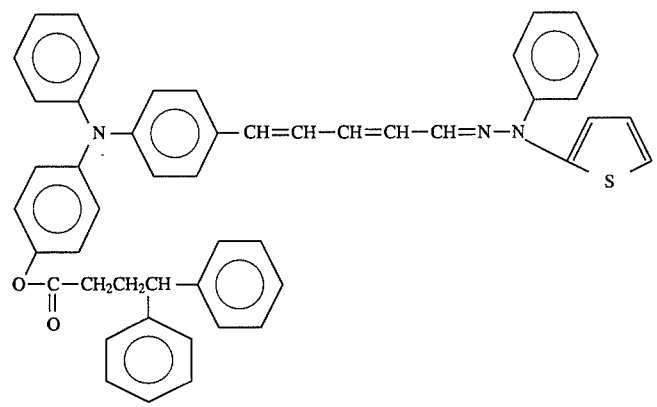
49
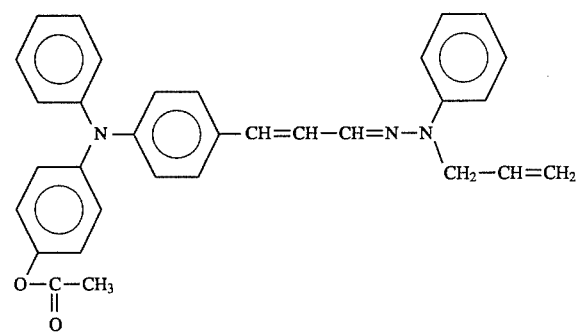
50
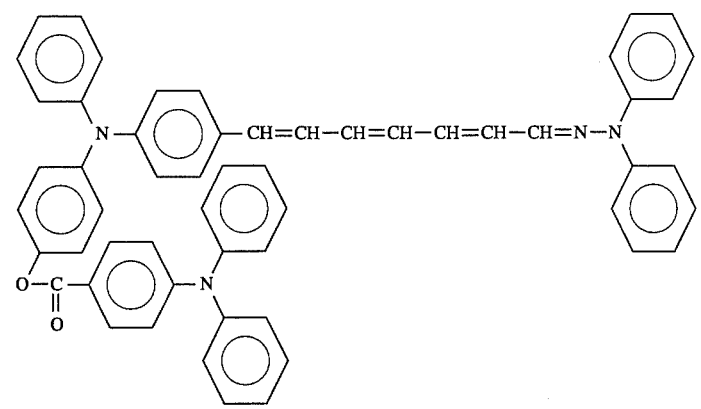
51

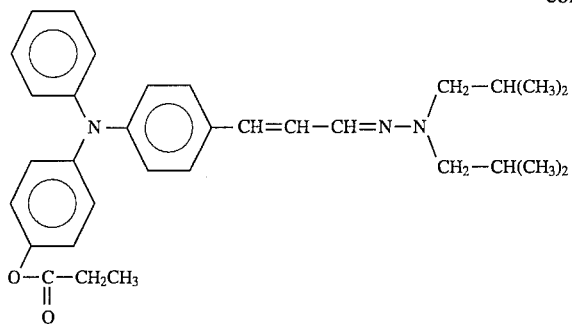
52
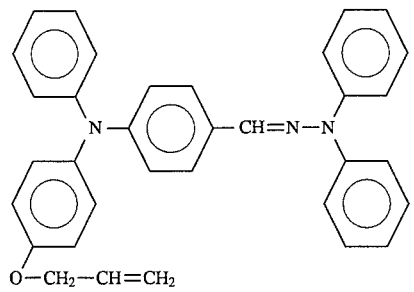
53
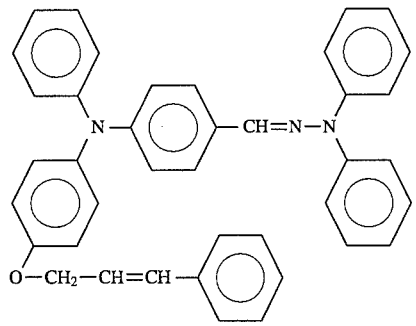
54
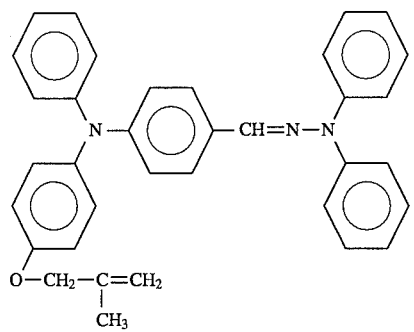
55
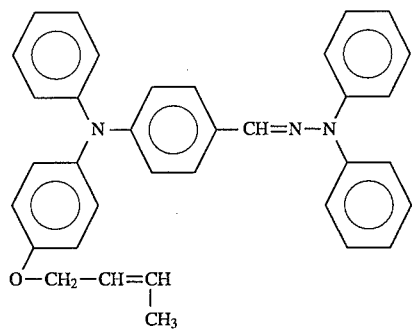
56
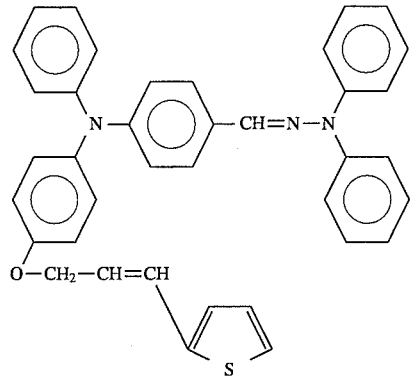
57
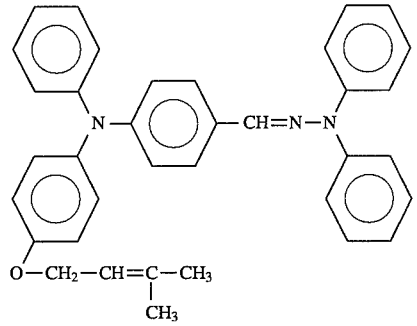
58

-continued
59
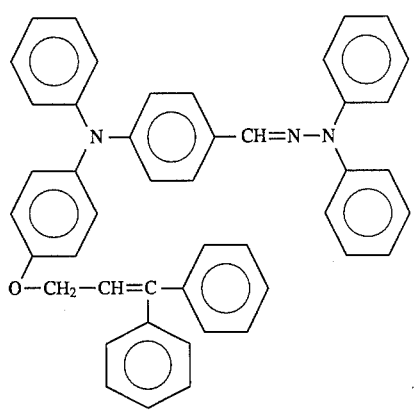
60
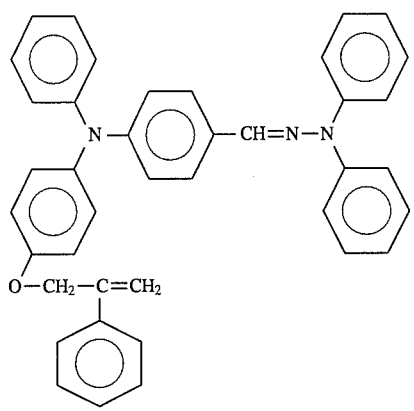
61
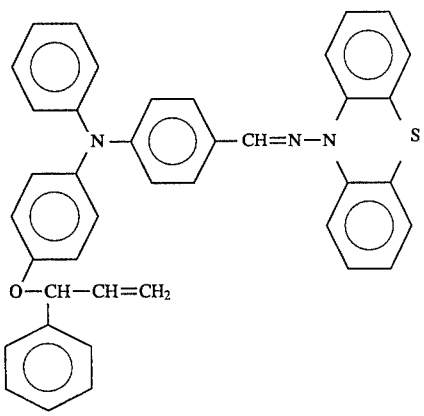
62
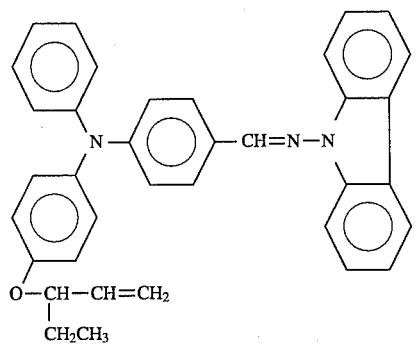
63
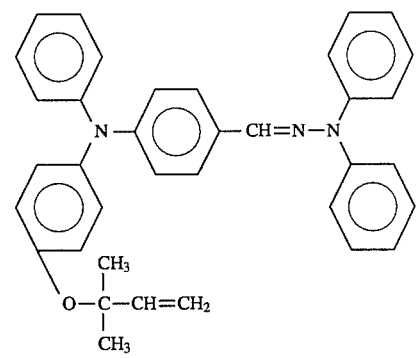
64
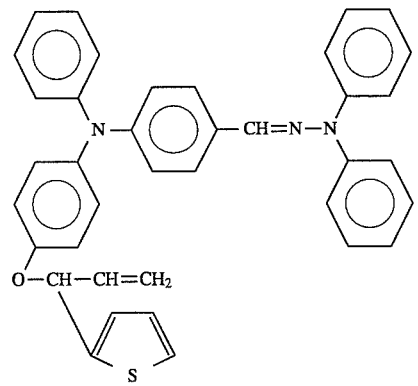
65
66
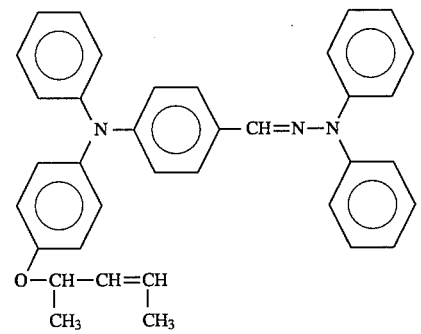

-continued
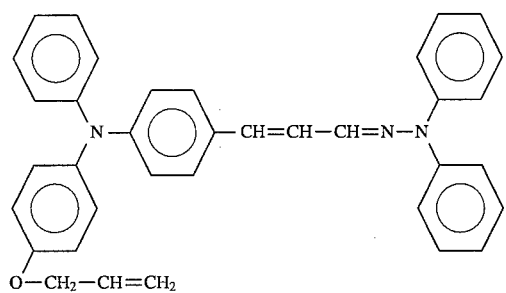
67
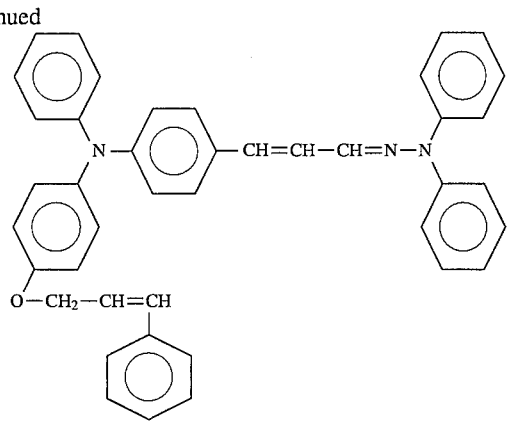
68
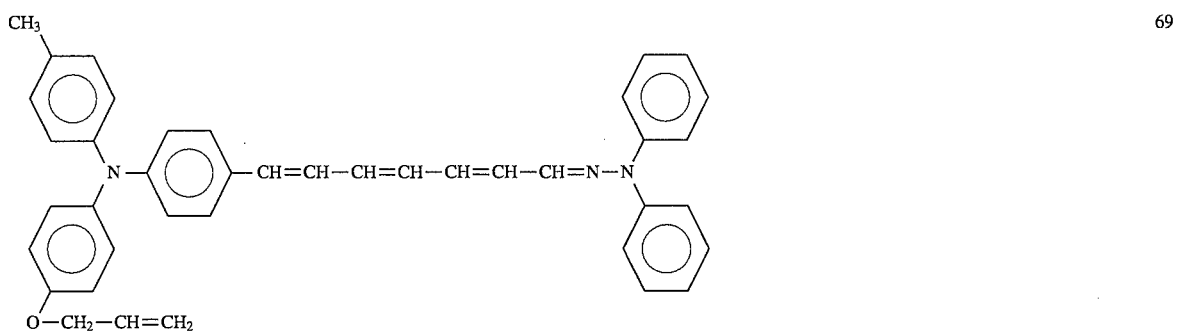
69
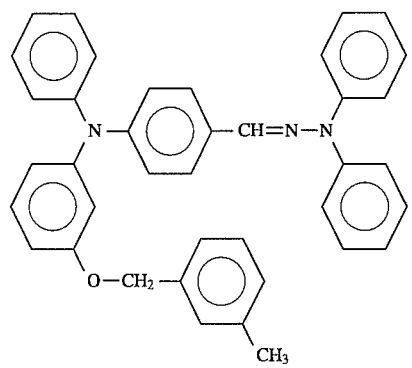
70
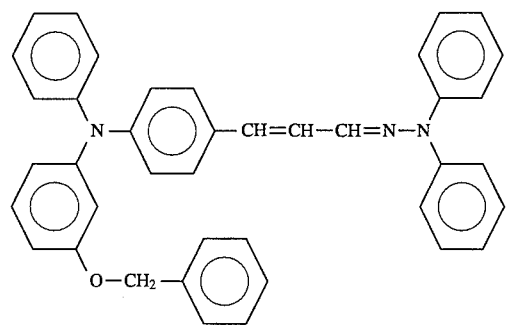
71
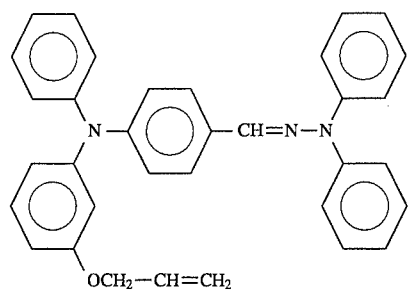
72
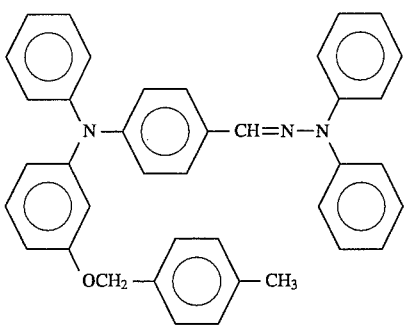
73

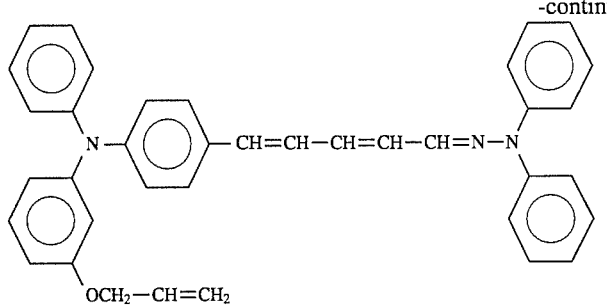

74

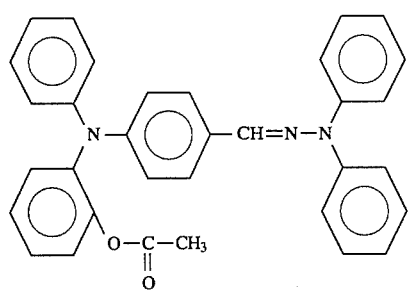

75

Arylamine hydrazone compounds of the general formula (I) above can be produced by means of anyone of well-known processes.

Preferred processes for the production of the above compounds are described by three cases as below:
(1) When A represents a group of the general formula (II);
(2) When A represents a group of the general formula (III);
(3) When A represents a group of the general formula (IV).

(1) When A represents a group of the general formula (II):

This type of compounds are produced by means of a process according to which a known arylamine compound is subjected to a known reaction for carbonyl introduction, then to a known reaction for etherification. Thereafter desired times of known wittig reactions followed by known reaction for carbonyl introduction are carried out and finally the obtained product is dehydrated with a desired hydrazine to give arylamine hydrazone compound. This process will now be explained more specifically in the following:

carbonyl introduction

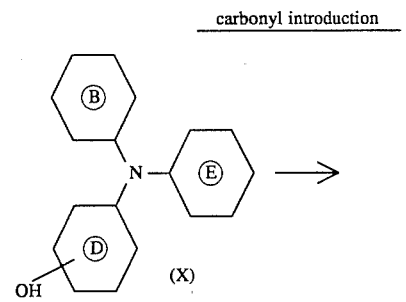

1. When R' is H:

An arylamine compound of the general formula (X) in which B, D and E are of the same meanings as defined in the general formula (I) is reacted with a formylation agent such as N,N-dimethylformamide or N-methylformanilide in the presence of phosphorus oxychloride to give an aldehyde of the general formula (XI) in which B, D and E are of the same meanings as defined in the general formula (I). Formylation agent may be used in largely excessive amount for serving also as reaction solvent, or a reaction inert solvent such as o-dichlorobenzene or benzene may be used.

2. When R' is not H:

An arylamine compound of the general formula (X) in which B, D and E are of the same meanings as defined in the general formula (I) is reacted with an acid chloride of the general formula Cl—CO—$R^1$ in the presence of a Lewis acid such as aluminium chloride, iron chloride or zinc chloride, in a solvent such as nitrobenzene, dichloromethane or carbon tetrachloride to give a ketone of the general formula (XI) in which B, D and E are of the same meanings as defined in the general formula (I).

etherification

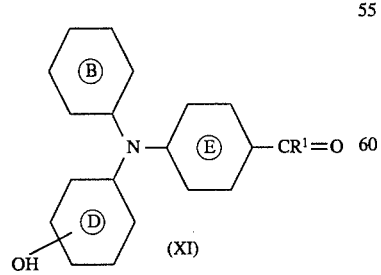

-continued
etherification

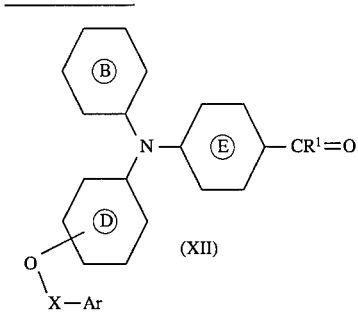

Then an arylamine compound of the general formula (XI) is reacted with a halide of the general formula W—X—Ar in which W represents a halogen atom such as chlorine, bromine or iodine atom, Ar and X are of the same meanings as defined in general formula (I), in the presence of a base such as potassium hydroxide, sodium hydroxide, pyridine or triethylamine, in a reaction inert solvent such as toluene, benzene, tetrahydrofuran, dioxane or N,N-dimethylformamide to give an arylamine compound of the general formula (XII) in which B, D, E, X, Ar and $R^1$ are of the same meanings as defined in the general formula (I).

witting reaction

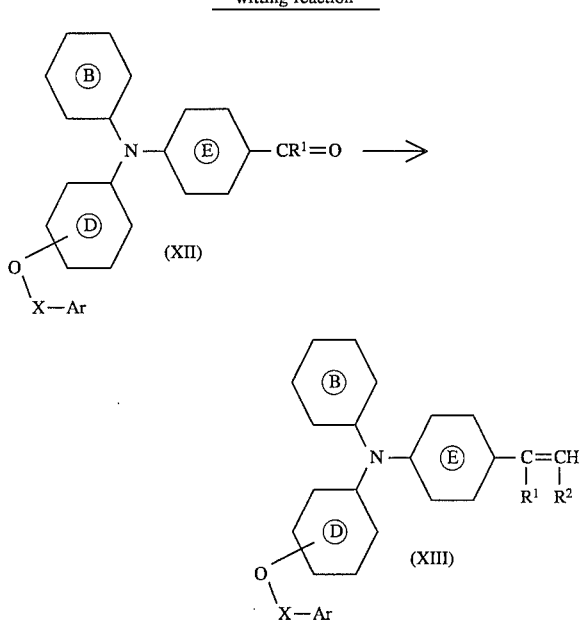

An arylamine compound of the general formula (XII) is reacted with a phosphonium salt of the general formula $[R_2—CH_2PPh_3]^+w^-$ in which w represents a halogen atom such as chlorine, bromine or iodine atom and Ph represents a phenyl group, in the presence of a base such as sodium methoxide or sodium hydride, in a reaction inert solvent such as N,N-dimethylformamide, dioxane, toluene, benzene or tetrahydrofuran to give an arylamine compound of the general formula (XIII) in which B, D, E, X, At, $R^1$ and $R^2$ and are of the same meanings as defined in the general formula (I).

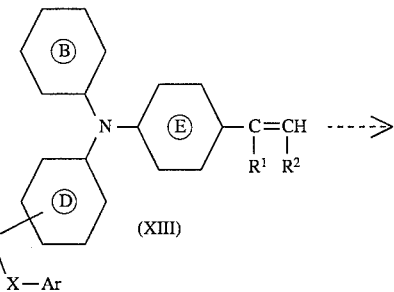

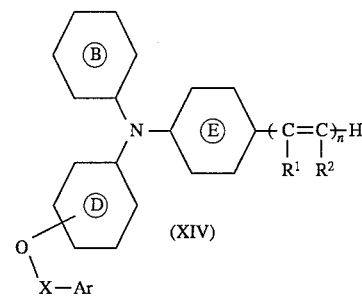

When $n \geq 2$, in the above described process for obtaining an arylamine compound of the general formula (XIII), the above described reaction for carbonyl introduction is followed by (n-1) times of the above described wittig reactions to give an arylamine compound of the general formula (XIV) in which B, D, E, $R^1$ and $R^2$ are of the same meanings as defined in the general formula (I).

carbonyl introduction

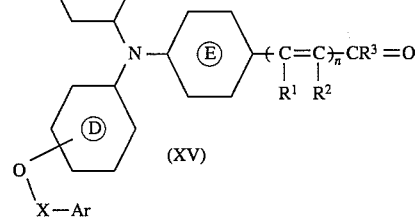

Thereafter, the arylamine compound of the general formula (XIV) is subjected to the above described reaction for carbonyl introduction to obtain an arylamine compound of the general formula (XV) in which B, D, E, X, Ar, $R^1$, $R^2$, $R^3$ and n are of the same meanings as defined in the general formula (I).

hydrazonation

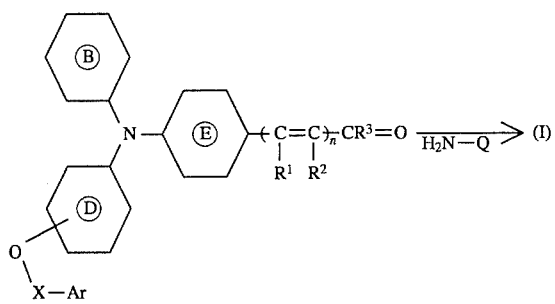

Finally, the obtained arylamine compound of the general formula (XV) is condensated with a hydrazine of the general formula H₂N—Q in which Q is of the same meaning as defined in the general formula (I) through dehydration to give an arylamine hydrazone compound of the general formula (I).

The condensation through dehydration may be conducted under heating of 50° C. to 150° C. as required, in a reaction inert solvent such as methanol, ethanol, tetrahydrofuran, cellosolve, N,N-dimethylformamide, benzene or toluene, and if desired, auxiliaries such as paratoluene sulfonic acid, hydrochloric acid or sodium acetate may be used for serving as reaction accelerator.

(2) When A represents a group of the general formula (III):

This type of compounds are produced by means of a process according to which a known arylamine compound is subjected to a known reaction for cabonyl introduction, then the desired times of known wittig reactions followed by a known reactions for carbonyl introduction are carried out. Thereafter a known esterification is performed and finally the obtained product is dehydrated with a desired hydrazine to give arylamine hydration compound. This process will now be explained more specifically in the following:

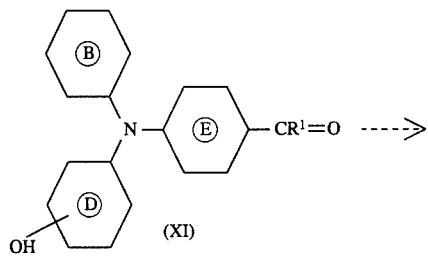

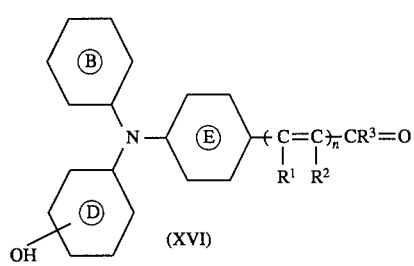

The arylamine compound of the general formula (XI) obtained through the above described reaction for carbonyl introduction is subjected to desired times of the above described wittig reactions followed by the above described reactions for carbonyl introduction to give an arylamine compound of the general formula (XVI) in which B, D, E, R¹, R², R³ and n are of the same meanings as defined in the general formula (I).

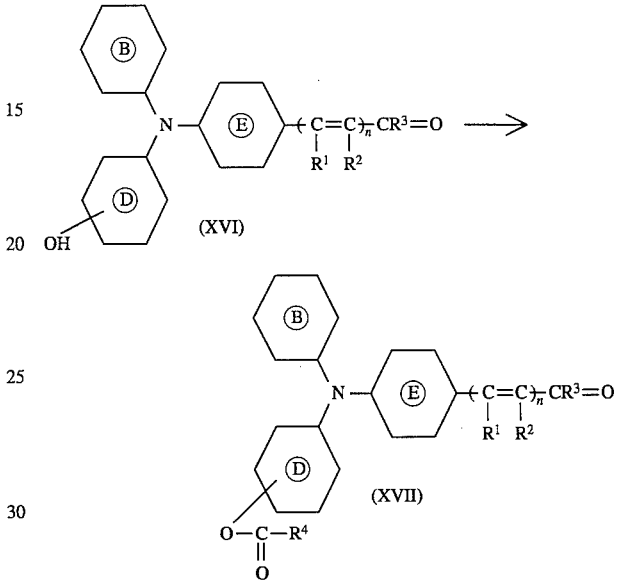

Then, the obtained arylamine compound of the general formula (XVI) is reacted with an acid chloride of the general formula Cl—CO—R⁴ in the presence of a base such as pyridine or triethylamine, in a reaction inert solvent such as toluene, benzene, tetrahydrofuran, dioxane or N,N-dimethylformamide to give an arylamine compound of the general formula (XVII) in which B, D, E, R¹, R², R³ and n are of the same meanings as defined in the general formula (I).

Finally, the obtained arylamine compound of the general formula (XVII) is subjected to the above described hydrazonation to give an arylamine hydrazone compound the general formula (I).

(3) When A represents a group of the general formula (IV):

1. When n is 0:

This type of compounds are produced by means of a process according to which a known arylamine compound is subjected to a known reaction for cabonyl introduction. Then a known etherification is carried out and finally the obtained product is dehydrated with a desired hydrazine to give arylamine hydration compound. This process will now be explained more specifically in the following.

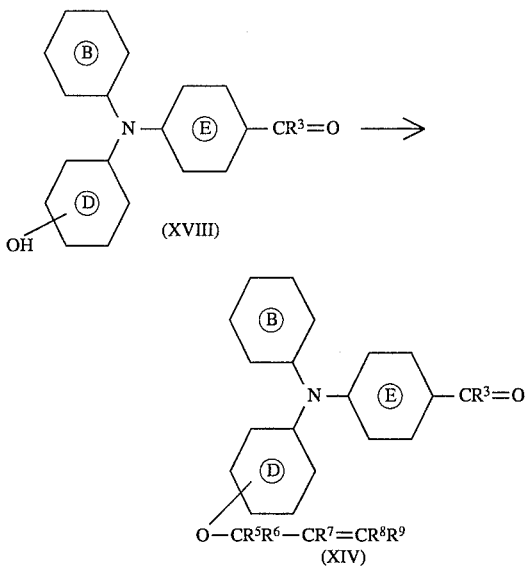

(XVIII)

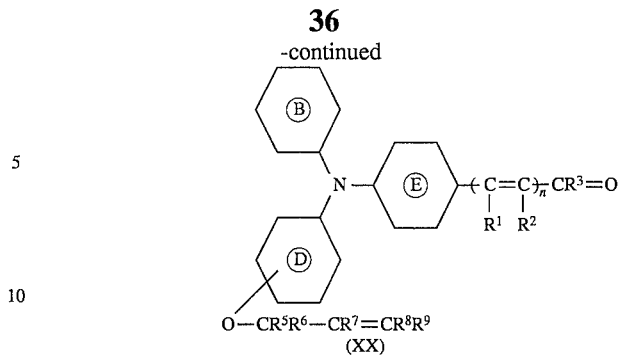

(XX)

The arylamine compound of the general formula (XVI) above is etherified with a halide of the general formula W—$CR^5R^6$—$CR^7$=$CR^8R^9$ above to give an arylamine compound of the general formula (XX) in which B, D, E, $R^1$, $R^2$, $R^3$, $R^5$, $R^6$, $R^7$, $R^8$ and $R^9$ are of the same meanings as defined in the general formula (I).

Finally, the obtained arylamine compound of the general formula (XX) is subjected to the above described hydrazonation to give an arylamine hydrazone compound of the general formula (I).

If desired, known purification process such as recrystallization, sublimation or column purification may be inserted after each reaction step or performed after all reaction steps to obtain a highly pure compound.

An electrophotographic photoreceptor according to the present invention comprises a photosensitive layer which contains at least one of the arylamine hydrazone compounds of the general formula (I) set forth hereinbefore.

Arylamine hydrazone compounds of the general formula (I) exhibit a very excellent performance as organic photoconducor. These compounds could give a photoreceptor having a high sensitivity and a good durability particularly when used as charge transport medium.

In an electrophotographic photoreceptor, various forms of photosensitive layers are known in the art and any of these known forms may be used for the photosensitive layers in the electrophotographic photoreceptor of the present invention. There may be mentioned: a photosensitive layer containing an arylamine hydrazone compound in a binder together with a colorant acting as sensitizer and an electron attractive compound both being added thereto at need; a photosensitive layer containing in a binder an arylamine hydrazone compound and photoconductive particles able to generate charge carriers with a very high efficiency on absorption of light; or a laminated photosensitive layer comprising a charge transport layer and a charge generate layer, the former layer consisting of an arylamine hydrazone compound and a binder, the latter layer containing photoconductive particles able to generate charge carriers on absorption of light optionally together with a binder.

In order to form these photosensitive layers, other known arylamine compounds, hydrazone compounds, stilbene compounds and the like which exhibit an excellent performance as organic photoconductor may be mixed with arylamine hydrazone compounds of the general forumla (I).

According to the present invention, when the photosensitive layer is prepared in the form of a two-layered system consisting of a charge layer and a charge transport layer and when an arylamine hydrazone compound of the general formula (I) is contained in the charge transport layer, there could be obtained a photoreceptor which exhibits a high sensitivity and a low residual potential, and, which, on repeated use or exposure to intense light, minimizes the changes in surface voltage and sensitivity as well as the (XIV)

The arylamine compound of the general formula (XVII) obtained through the above described reaction for carbonyl introduction in which B, D, E and $R^3$ are of the same meanings as defined in the general formula (I) is etherified with a halide of the general formula W—$CR^5R^6$—$CR^7$=$CR^8R^9$ in which W represents a halogen atom such as chlorine, bromine or iodine atoms, and $R^5$, $R^6$, $R^7$, $R^8$ and $R^9$ are of the same meanings as defined in the general formula (I) to give an arylamine compound of the general formula (XIV) in which B, D, E, $R^3$, $R^5$, $R^6$, $R^7$, $R^8$ and $R^9$ are of the same meanings as defined in the general formula (I).

Finally, the obtained arylamine compound of the general formula (XIV) is subjected to the above described hydrazonation to give an arylamine hydrazone compound of the general formula (I).

2. When n is not 1:

This type of compounds are produced by means of a process according to which a known arylamine compound is subjected to a known reaction for carbonyl introduction, then desired times of known wittig reactions followed by a known carbonyl reaction for introduction are carried out and finally the obtained product is dehydrated with a desired hydrazine to give arylamine hydration compound. This process will be now explained more specifically in the following;

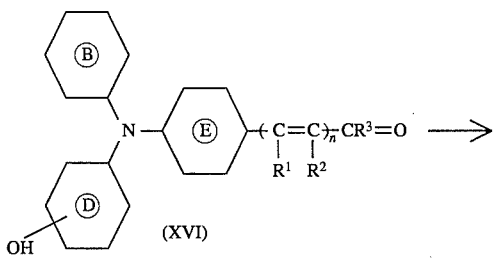

(XVI)

accumulation of residual potential, thus is excellent in durability.

An electrophotographic photoreceptor of the present invention may be fabricated by means of any conventional procedure. In fact, an arylamine hydrazone compound of the general formula (I) is dissolved in a suitable solvent together with a binder. To the obtained mixture, photoconductive particles able to generate charge carriers with a very high efficiency on absorption of light, a sensitizing dye, an electron attractive compound and other additives such as plasticizer or pigment are optionally added to obtain a coating solution. The obtained coating solution is applied onto a conductive support and the obtained coating is dried to form a photosensitive layer of usually several to several tens of μm thick, preferably 10 to 40 μm thick. When a photosensitive layer is prepared in the form of a two-layered system consisting of a charge generate layer and a charge transport layer, the photosensitive layer may be formed by applying the said coating solution on the charge generate layer or by forming a charge generate layer on the charge transport layer obtained by the application of the said coating solution.

Solvents which may be used to prepare the coating solution are those which could dissolve arylamine hydrazone compounds and may be mentioned: ethers such as tetrahydrofuran and 1,4-dioxane; ketones such as methylethylketone and cyclohexanone; aromatic hydrocarbons such as toluene and xylene; aprotic polar solvents such as N,N-dimethyl formamide, acetonitorile, N-methyl pyrrolidone and dimethyl sulfoxide; esters such as ethyl acetate, methyl formate and methyl cellosolve acetate; chlorinated hydrocarbons such as dichloroethane and chloroform. Among these solvents, those which could dissolve binders should naturally be selected. Binders which may be used include: polymers and copolymers of vinyl compounds such as styrene, vinyl acetate, vinyl chloride, ester acrylate, ester methacrylate and butadiene; various polymers compatible with styrene compounds such as polyvinyl acetal, polycarbonate, polyester, polysulfone, polyphenylene oxide, polyurethane, cellulose ester, cellulose ether, phenoxy resin, silicone resin and epoxy resin. Binders are used at a weight ratio of normally 0.5 to 30, preferably 0.7 to 10 based on the arylamine hydrazone compounds.

Photoconductive particles, dyestuffs and electron attractive compounds which may be admixed into the above mentioned photosensitive layer could be selected from those well known in the art. Photoconductive particles able to generate charge carriers with a very high efficiency on absorption of light may include: inorganic photoconductive particles such as selenium, selenium-tellurium alloy, selenium-arsenic alloy, cadmiun sulfide, amorphous silicon; and organic photoconductive particles such as metal-containing phthalocyanine, perinone pigments, thioindigo, quinacridone, perylene pigments, anthraquinone pigments, azo pigments, bis-azo pigments, tris-azo pigments, tetrakis-azo pigments and cyanine pigments. When combined with metal-containing phthalocyanine, there could be obtained an excellent photosensitive layer having an improved sensitivity to laser light and a decreased residual potential.

Examples of dyes which may be mentioned are: triphenylmethane dyes such as Methyl Violet, Brilliant Green and Crystal Violet; thiazine dyes such as Methylene Blue; quinone dyes such as Quinizarine; cyanine dyes; pyrylium salts; thiapyrylium salts; and benzopyrylium salts. Examples of electron attractive compounds able to form a charge transport complex with an arylamine hydrazone compound are: quinones such as chloranil, 2,3-dichloro-1,4-naphthoquinone, 1-nitroanthraquinone, 1-chloro-5-nitroanthraquinone, 2-chloroanthraquinone and phenanthrenequinone; aldehydes such as 4-nitrobenzaldehyde ketones such as 9-benzoylanthracene, indandione, 3,5-dinitrobenzophenone, 2,4,7-trinitrofluorenone, 2,4,5,7-tetranitrofluorenone and 3,3',5,5'-tetranitrobenzophenone; acid anhydrides such as anhydrous phthalic acid and anhydrous 4-chloronaphthalic acid; cyano compounds such as tetracyano ethylene, terephtalalmalononitrile, 9-anthrylmethylydenemalononitrile, 4-nitrobenzalmalononitrile and 4-(p-nitrobenzoyloxy)-benzalmalononitrile; phthalides such as 3-benzalphthalide, 3-(α-cyano-p-nitrobenzal)phthalide and 3-(α-cyano-p-nitrobenzal)-4,5,6,7-tetrachlorophthalide.

Moreover, in the electrophotographic photoreceptor of the present invention, the photosensitive layer may contain a well known plasticizer for improving the film-formation property, the flexibility and the mechanical strength thereof. Plasticizers which can be admixed into the above mentioned coating solution include: phthalic ester, phosphoric ester, epoxy compound, chlorinated paraffin, chlorinated fatty acid ester, aromatic compounds such as methylnaphtalene. When an arylamine hydrazone compound is used as charge transport medium in the charge transport layer, the coating solution could have the above mentioned composition, but photoconductive particles, dyestuffs and electron attractive compounds therein may be omitted or used in a small amount. In this type of photosensitive layers, the charge generation layer may be formed by applying a coating solution prepared by dissolving or dispersing the above mentioned photoconductive particles in a solvent optionally together with binder polymers, organic photoconductive substances, dyestuffs or electron attractive compounds and then drying to obtain a thin film. Alternatively, it may be formed by depositing the photoconductive particles by means of a suitable way such as vapor deposition to obtain a thin film.

Furthermore, in the electrophotographic photoreceptor of the present invention, the photosensitive layer may contain other well known additives for improving the electrical properties and the durability on repeated use. For these purposes, phenolic compounds, organic phosphor compounds, organic sulfur compounds and the like may be admixed to the above mentioned coating solution.

It is obvious that the photoreceptor thus formed may further comprise a bonding layer, an intermediate layer, a transparent insulating layer and the like as required. A conductive support onto which the photosensitive layer is formed may be any of well known materials used for the fabrication of electrophotographic photoreceptors. Materials which may be mentioned are metals such as aluminium, stainless steel and copper in the form of drum or sheet. Laminate of mettalic foils or metallized deposit consisting of these metals may also be used. Other materials which may be mentioned are plastic film, plastic drum, paper and paper tube each made conductive by means of conductive substances such as metal powder, carbon black, copper iodide or high molecular electrolyte which was applicated thereonto together with a suitable binder. Plastic sheet or drum made conductive through the incorporation of conductive substance such as metal powder, carbon black or carbon fiber may also be used.

The effects of the invention

The electrophotographic photoreceptor of the present invention exhibits a very high sensitivity and a lowering in residual potential which would cause foggy images. It is also advantageous in that, because of diminished photo-fatigue thereof, the accumulation of residual potential, the changes in surface voltage and sensitivity variation on repeated use or at intense exposure could be minimized, hence excellent in durability.

Examples

The present invention will now be described in more detail by way of examples. These preparations and examples should be considered by no means limitative without departing from the spirits of the present invention. The term "parts" herein used denotes "parts by weight".

Preparation 1

(p-hydroxy)diphenylamine

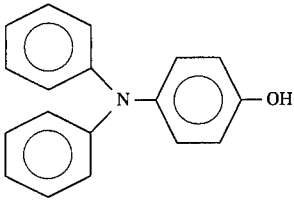

5.2 g of the compound of the above formula was dissolved in 20 ml of N,N-dimethylformamide, then 5.5 ml of phosphorus oxychloride was added thereto, and thereafter the reaction was carried out at 65° C. for 5 hours.

After allowed to cool, the reaction liquid was taken into 100 ml of ice water and hydrolysed with sodium hydroxide, then extracted, concentrated and purified according to conventional procedures to obtain 5.4 g of formyl compound represented by the following formula:

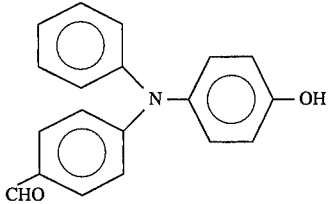

2.0 g of the obtained formyl compound, 1.2 g of benzylbromide and 0.2 g of tetra-n-butylammonium bromide were dissolved in 20 ml of tetrahydrofuran, 0.6 g of sodium hydroxide was added thereto and the reaction was carried out at 60° C. for 2 hours.

After allowed to cool, the reaction liquid was poured into 100 ml of ice water, then extracted, concentrated and purified according to conventional procedures to obtain 2.5 g of arylamine compound represented by the following formula:

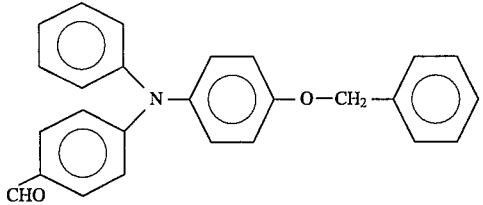

Then, 2.5 g of the obtained arylamine compound was reacted with 1.8 g of 1,1-diphenylhydrazine in the presence acetic acid catalyst, in the mixed solvent of 40 ml of tetrahydrofuran and 30 ml of methanol at 60° C. for 5 hours. After allowed to cool, the reaction liquid was taken into 200 ml of ice water, then extracted, concentrated and purified according to conventional procedures to obtain 3.1 g of yellow crystals (m.p. 154°–155° C.).

The results of elemental analysis set forth below and the infrared absorption spectrogram (FIG. 1) showed that the obtained compound was identified with the arylamine hydrazone compound represented by the formula of the Compound No. 1.

Elemental analysis for $C_{38}H_{31}N_3O$: Calculated values: C 83.64%; H 5.73%; N 7.70%: Found values: C 83.48%; H 5.70%; N 7.70%. Mass spectrometric analysis for $C_{38}H_{31}N_3O$: Mw=545 M$^+$=545

Preparation 2

2.0 g of the formyl compound obtained as the intermediate Preparation 1 and 0.8 ml of pyridine were dissolved in 30 ml of toluene, then 0.6 ml of acetyl chloride was added dropwise thereto. Thereafter, the reaction was carried out at 80° C. for 2 hours. After allowed to cool, the reaction liquid was taken into 100 ml of ice water, then extracted, concentrated and purified according to conventional procedures to obtain 2.1 g of the arylamine compound represented by the following formula:

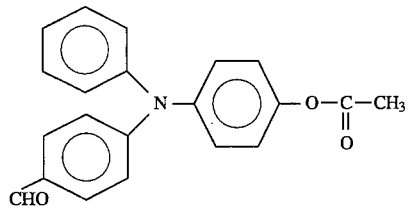

Then, 2.1 g of the obtained arylamine compound was reacted with 1.6 g of 1,1-diphenylhydrazine in the presence of acetic acid catalyst, in the mixed solvent of 30 ml of tetrahydrofuran and 25 ml of methanol at 60° C. for 5 hours. After allowed to cool, the reaction liquid was taken into 200 ml of ice water, then extracted, concentrated and purified according to conventional procedures to obtain 2.3 g of yellow crystals (m.p.132°–134° C.).

Figure 2:
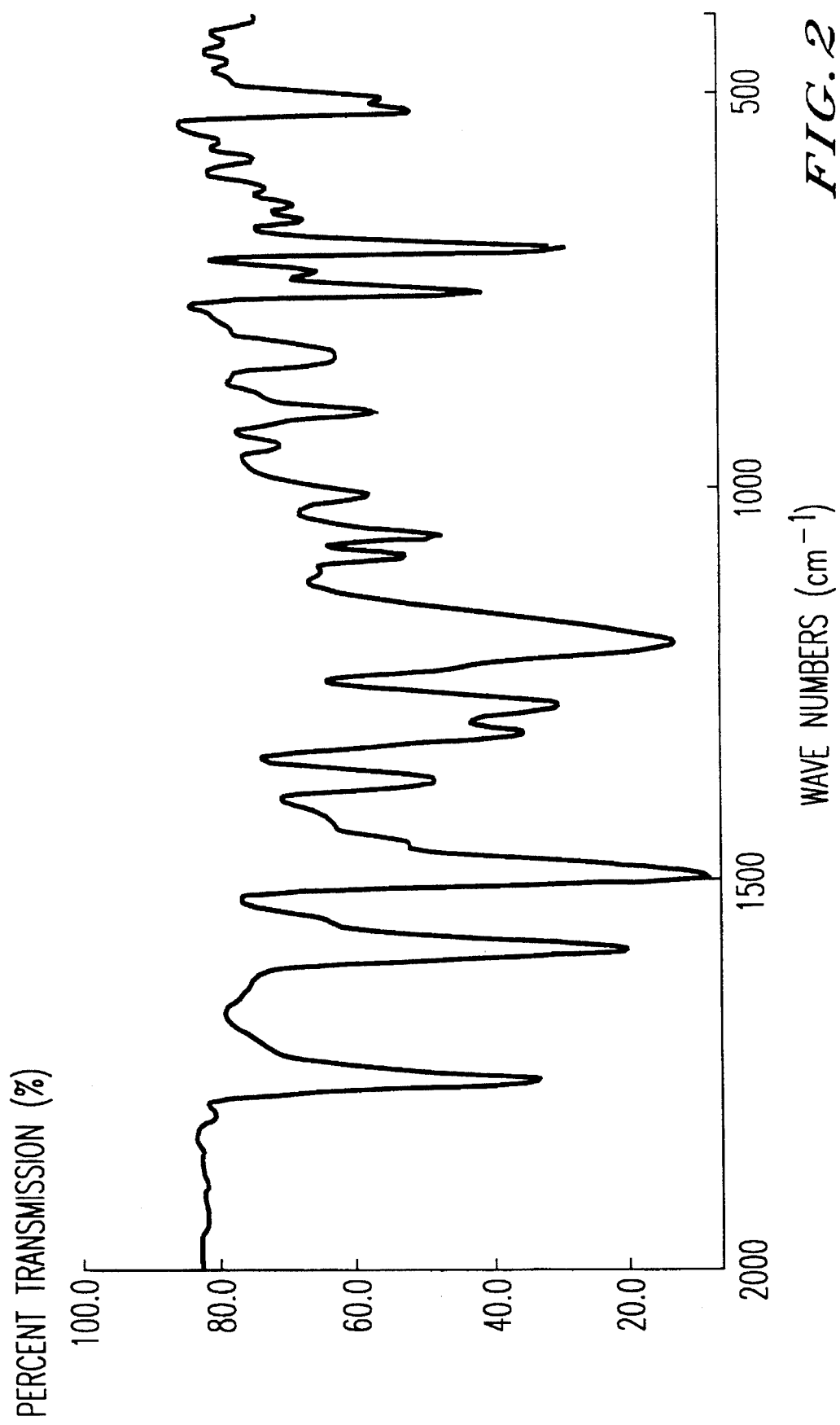

The results of elemental analysis set forth below and the infrared absorption spectrogram (FIG. 2) showed that the obtained compound was identified with the arylamine hydrazone compound represented by the formula of Compound No.13.

Elemental analysis for $C_{33}H_{27}N_3O_2$: Calculated values: C 79.66%; H 5.47%; N 8.44%: Found values: C 79.49%; H 5.46%; N 8.43%. Mass spectrometric analysis for $C_{33}H_{27}N_3O_2$: Mw=497 M$^+$=497

Preparation 3

2.0 g of the formyl compound obtained as the intermediate of Preparation 1, 1.3 g of α-bromo-p-xylene and 0.2 g of tetra-n-butylammonium bromide were dissolved in 20 ml of tetrahydrofuran, 0.6 ml of potassium hydroxide was added thereto, then the reaction was carried out at 60° C. for 2 hours.

After allowed to cool, the reaction liquid was taken into 100 ml of ice water, then extracted, concentrated and purified according to conventional procedures to obtain 2.5 g of the arylamine compound represented by the following formula:

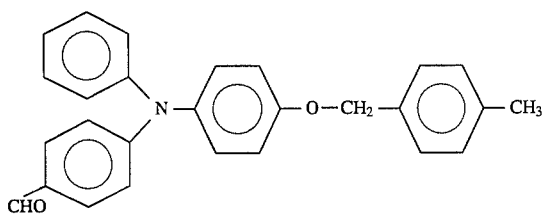

Then, 2.3 g of triphenylphosphine was dissolved in 100 ml of N,N-dimethylformamide, then 1.9 g of methyl iodide was added dropwise thereto to produce a phosphonium salt, into which 2.5 g of the obtained arylamine compound was added and then 0.9 g of sodium methylate was added by portions, thereafter the reaction was carried out at 50° C. for 2 hours.

After allowed to cool, the reaction liquid was taken into 50 ml of ice water, then extracted, concentrated and purified according to conventional procedures to obtain 2.1 g of the arylamine compound represented by the following formula:

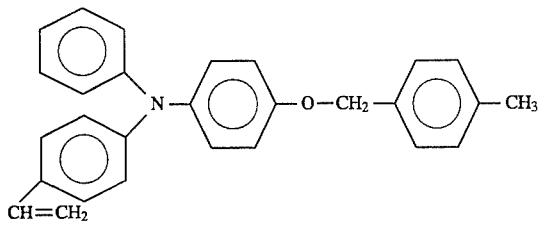

2.1 g of the obtained arylamine compound was dissolved in 23 ml of N,N-dimethylformamide, 0.6 ml of phosphorus oxychloride was added thereto, and thereafter the reaction was carried out at 60° C. for 3 hours. After allowed to cool, the reaction liquid was taken into 50 ml of ice water and hydrolysed with sodium hydroxide, then extracted, concentrated and purified according to conventional procedures to obtain 2.1 g of the arylamine compound represented by the following formula:

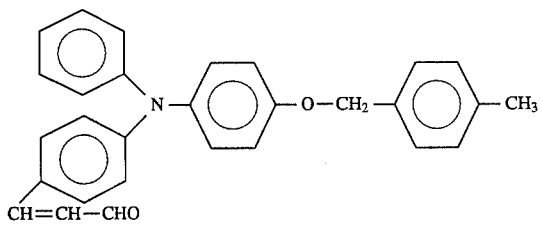

Figure 3:
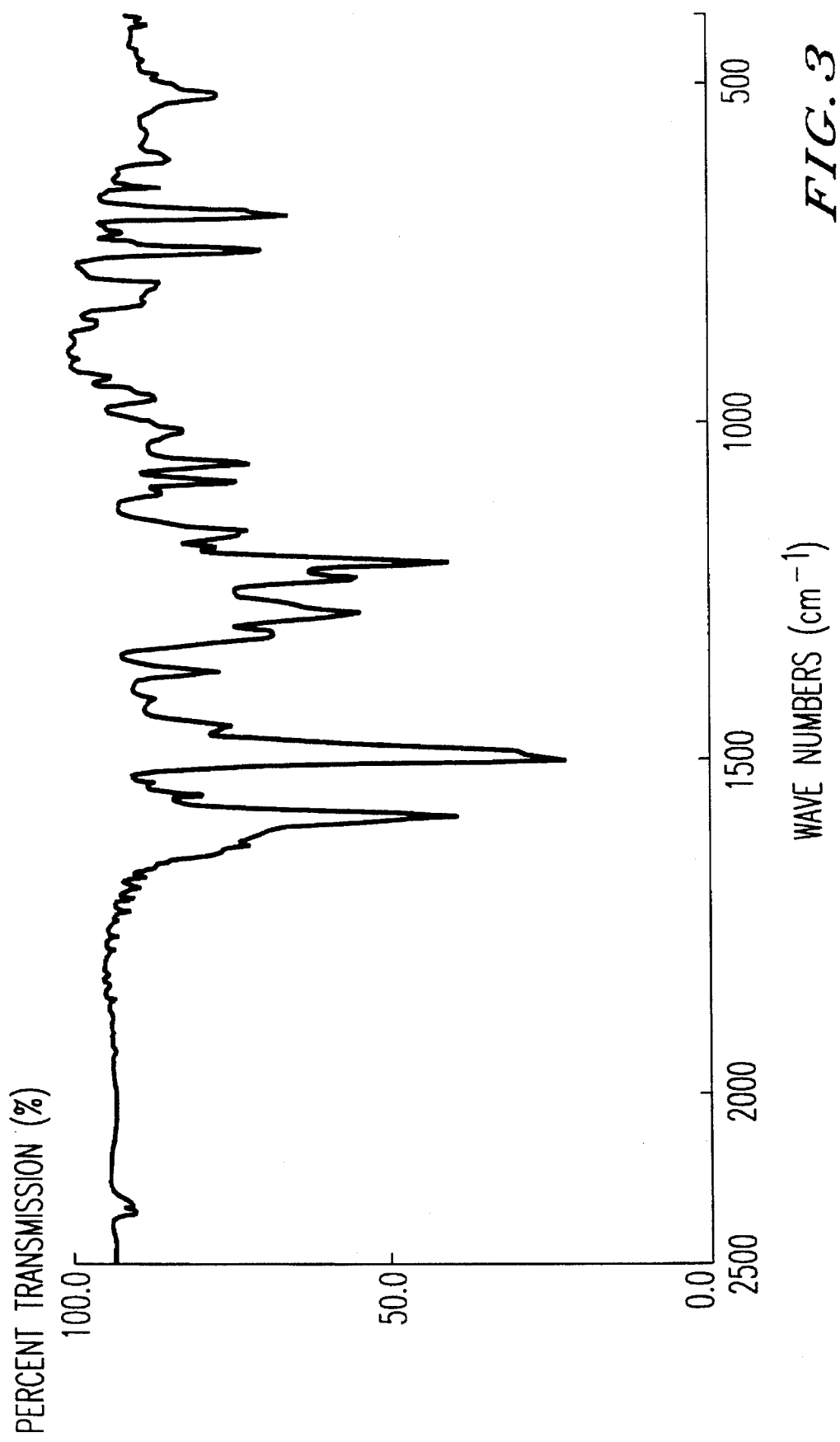

Then, 2.1 g of the obtained arylamine compound was reacted with 1.4 g of 1,1-diphenylhydrazine in the presence of acetic acid catalyst, in the mixed solvent of 30 ml of tetrahydrofuran and 25 ml of methanol at 60° C. for 5 hours. After allowed to cool, the reaction liquid was taken into 150 ml of ice water, then extracted, concentrated and purified according to conventional procedures to obtain 2.8 g of yellow crystals (m.p. 159°–161° C.). The results of elemental analysis set forth below and the infrared absorption spectrogram (FIG. 3) showed that the obtained compound was identified with the arylamine hydrazone compound represented by the formula of the Compound No. 28.

Elemental analysis for $C_{41}H_{35}N_3O$: Calculated values: C 84.07%; H 6.02%; N 4.78%: Found values: C 83.98%; H 6.00%; N 4.73%. Mass spectrometric analysis for $C_{41}H_{35}N_3O$: Mw=585 Mw$^+$=585

Preparation 4

2.7 g of triphenylphosphine was dissolved in 7 ml of N,N-dimethylformamide, then 2.1 g of methyl iodide was added dropwise thereto. Then, 2.0 g of the formyl compound obtained as the intermediate of Preparation 1 was added, then 3.7 g of 28% sodium methylate in methanol was added dropwise. Thereafter, the reaction was carried out at 50° C. for 2 hours. After allowed to cool, the reaction liquid was taken into 100 ml of ice water, then extracted, concentrated and purified according to conventional procedures to obtain 1.8 g of the arylamine compound represented by the following formula:

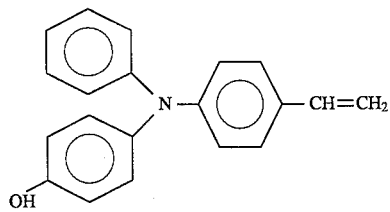

Then, 1.8 g of the obtained arylamine compound was dissolved in 20 ml of N,N-dimethylformamide, 2.8 ml of phosphorus oxychloride was added thereto, and thereafter the reaction was carried out at 60° C. for 3 hours. After allowed to cool, the reaction liquid was taken into 50 ml of ice water and hydrolysed with sodium hydroxide, then extracted, concentrated and purified according to conventional procedures to obtain 1.9 g of the arylamine compound represented by the following formula:

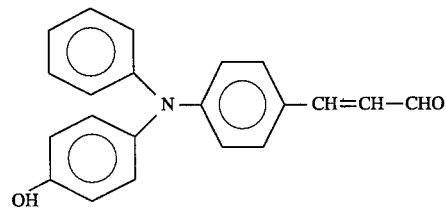

Then, 1.9 g of the obtained arylamine compound and 1.0 ml of pyridine were dissolved in 30 ml of toluene, and 0.5 ml of enanthyl chloride was added dropwise thereto. Thereafter, the reaction was carried out at 80° C. for 2 hours. After allowed to cool, the reaction liquid was taken into 100 ml of ice water and then extracted, concentrated and purified according to conventional procedures to obtain 2.0 g of the arylamine compound represented by the following formula:

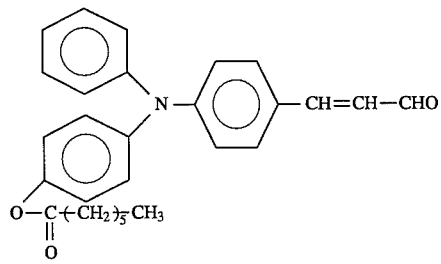

Then, 2.0 g of the obtained arylamine compound was reacted with 1.3 g of 1,1-diphenylhydrazine in the presence of acetic acid catalyst, in the mixed solvent of 30 ml of tetrahydrofuran and 25 ml of methanol at 60° C. for 5 hours. After allowed to cool, the reaction liquid was taken into 150 ml of ice water, then extracted, concentrated and purified according to conventional procedures to obtain 2.3 g of yellow oily product.

The results of elemental analysis set forth below and the infrared absorption spectrogram showed that the obtained compound was identified with the arylamine hydrazone compound represented by the formula of Compound No. 43.

Elemental analysis for $C_{40}H_{39}N_3O_2$: Calculated values: C 80.91%; H 6.62%; N 7.08%: Found values: C 80.86%; H 6.59%; N 7.06%. Mass spectrometric analysis for $C_{40}H_{39}N_3O_2$: Mw=593 M$^+$=593

Preparation 5

2.0 g of the formyl compound obtained as the intermediate of Preparation 1, 0.9 g of allyl bromide and 0.2 g of tetra-n-butylammonium bromide were dissolved in 20 ml of tetrahydrofuran, 0.6 g of potassium hydroxide was added thereto, then the reaction was carried out at 60° C. for 2 hours.

After allowed to cool, the reaction liquid was taken into 100 ml of ice water, then extracted, concentrated and purified according to conventional procedures to obtain 2.2 g of the arylamine compound represented by the following formula:

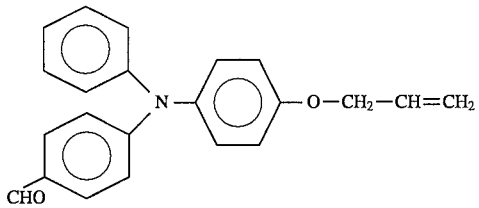

Then, 2.2 g of the obtained arylamine compound was reacted with 1.9 g of 1,1-diphenylhydrazine in the presence of acetic acid catalyst, in the mixed solvent of 40 ml of tetrahydrofuran and 30 ml of methanol at 60° C. for 5 hours. After allowed to cool, the reaction liquid was taken into 200 ml of ice water, then extracted, concentrated and purified according to conventional procedures to obtain 3.1 g of yellow crystals (m.p.123°–124.5° C.).

Figure 4:
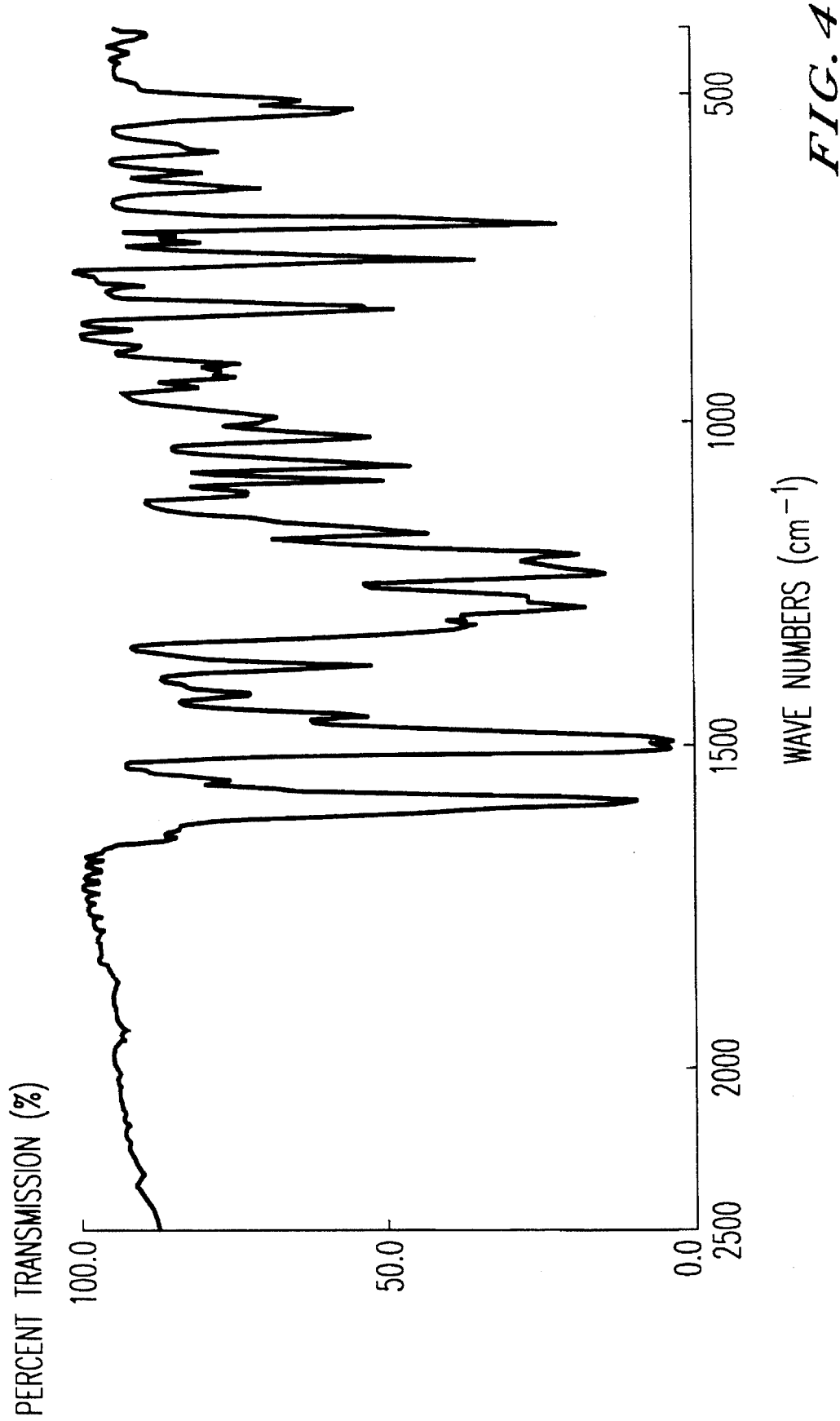

The results of elemental analysis set forth below and the infrared absorption spectrogram (FIG. 4) showed that the obtained compound was identified with the arylamine hydrazone compound represented by the formula of Compound No. 53.

Elemental analysis for $C_{34}H_{29}N_3O$: Calculated values: C 82.40%; H 5.90%; N 8.48%: Found values: C 82.29%; H 5.88%; N 8.45%. Mass spectrometric analysis for $C_{34}H_{29}N_3O$: Mw=495 M$^+$=495

Preparation 6

1.9 g of the arylamine compound obtained as the intermediate of Preparation 4, 0.8 g of allyl bromide and 0.2 g of tetra-n-butylammonium bromide were dissolved in 20 ml of tetrahydrofuran, 0.7 g of potassium hydroxide was added thereto, then the reaction was carried out at 60° C. for 2 hours.

After allowed to cool, the reaction liquid was taken into 100 ml of ice water, then extracted, concentrated and purified according to conventional procedures to obtain 2.1 g of the arylamine compound represented by the following formula:

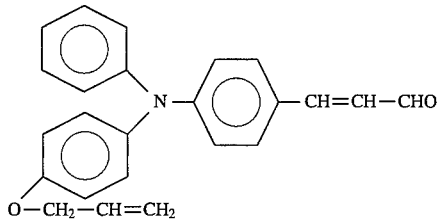

Then, 2.1 g of the obtained arylamine compound was reacted with 1.9 g of 1,1-diphenylhydrazine in the presence of acetic acid catalyst, in the mixed solvent of 40 ml of tetrahydrofuran and 30 ml of methanol at 60° C. for 5 hours. After allowed to cool, the reaction liquid was taken into 200 ml of ice water, then extracted, concentrated and purified according to conventional procedures to obtain 2.2 g of yellow crystals (m.p.78°–80° C.).

Figure 5:
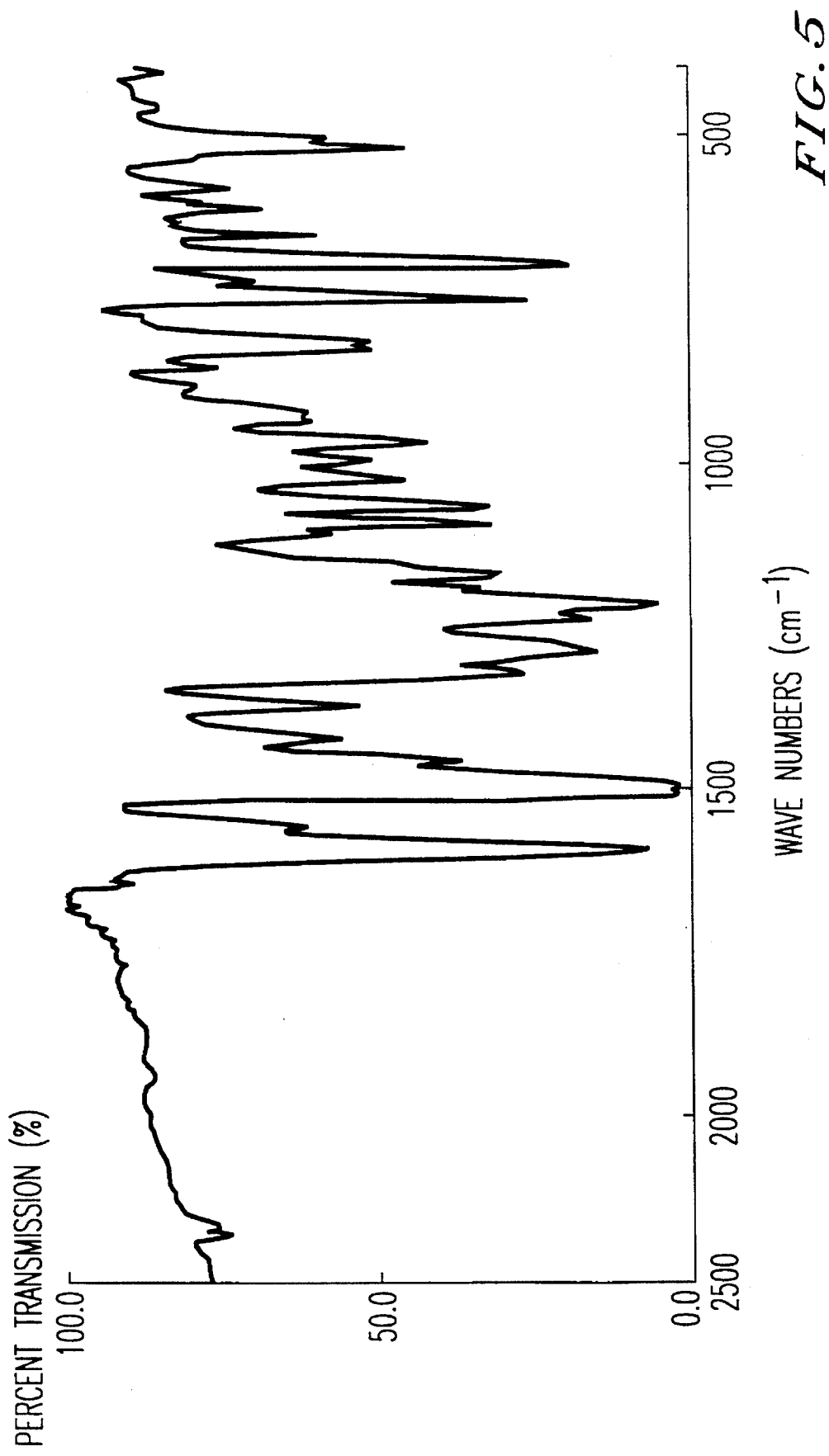

The results of elemental analysis set forth below and the infrared absorption spectrogram (FIG. 5) showed that the obtained compound was identified with the arylamine hydrazone compound represented by the formula of Compound No. 67.

Elemental analysis for $C_{36}H_{31}N_3O$: Calculated values: C 82.90%; H 5.99%; N 8.06%: Found values: C 82.20%; H 5.97%; N 8.05%. Mass spectrometric analysis for $C_{36}H_{31}N_3O$: Mw=521 M$^+$=521

Example 1

1.0 part of titanium oxyphthalocyanine pigment exhibiting strong diffraction peaks at Bragg angles (2θ±0.2°) 9.3°, 10.6°, 13.2°, 15.1°, 15.7°, 16.1°, 20.8°, 23.8° and 27.1° was added to 14 parts of dimethoxyethane, then made to disperse by means of a sand grinder. The obtained dispersion was diluted by adding 14 parts of dimethoxyethane and 14 parts of 4-methoxy-4-methylpentanone-2 (available from Mitsubishi Kasei Corporation), and thereafter dispersed into a solution prepared by dissolving 0.5 part of polyvinyl butyral (trade name "Denkabutyral #6000-C", available from Denki Kagaku Kogyo K.K.) and 0.5 part of phenoxy resin (trade name "UCAR® PKHH" available from Union Carbide Inc.,) in mixed solvent consisting of 6 parts of dimethoxyethane and 6 parts of 4-methoxy-4-methylpentanone-2. The obtained dispersion was applied by means of a wire bar onto aluminum layer deposited on a polyester film of 75 μm thick in an amount corresponding to 0.4 g/m$^2$ dry weight, and then dried to form a charge generate layer.

70 parts of arylamine hydrazone compound (Compound No. 1) and 100 parts of polycarbonate resin of the formula below:

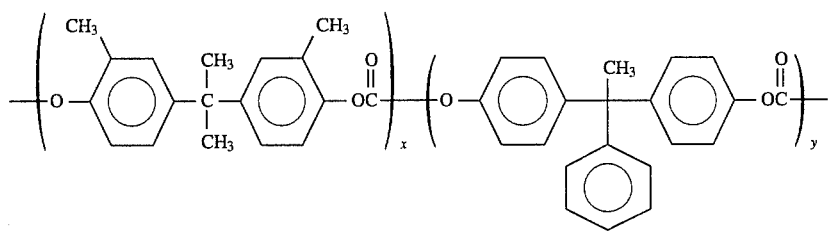

x:y = 1:1 were dissolved in a mixed solvent consisting of 585 parts of tetrahydrofuran and 315 parts of dioxane to prepare a coating solution. The prepared coating solution was applied onto the previously formed charge generate layer, and then dried to form a charge transport layer of 17 μm thick.

The electrophotographic photoreceptor provided with thus formed two-layered photosensitive layer was tested for sensitivity and the sesitivity was found as a half decay exposure of 0.49 μJ/cm².

The half decay exposure was determined as follows: first, the photoreceptor was negatively charged by means of 50 μA corona current in the dark. Then it was exposed to 780 nm light (exposure energy of 10 μW/cm²) obtained by passing 20 lux white light through an interference filter. This was to measure the exposure required for the surface voltage to attenuate from −450 V to −225 V.

The residual potential represented by the surface voltage at exposure time of 9.9 seconds was found to be −5V. After repeated 2000 cycles of the above processes, it was not observed any rise of the residual potential.

Example 2

An electrophotographic photoreceptor was fabricated in a similar manner as Example 1, except that the titanium oxyphthalocyanine pigment used in Example 1 was replaced by the titanium oxyphthalocyanine pigment exhibiting strong diffraction peaks at Bragg angles (2θ±0.2°) 9.5°, 27.1° and 27.3°. Thus obtained electrophotographic photoreceptor was tested for sensitibity by exposing it to light at 780 nm and the hale value decay exposure was found to be 0.13 μJ/cm².

Example 3

An electrophotographic photoreceptor was fabricated in a similar manner as Example 1, except that the titanium oxyphthalocyanine pigment used in Example 1 was replaced by naphthal bis-azo pigment represented by the formula below. Thus obtained electro-photographic photoreceptor was tested for sensitibity by exposing it to white light and the half decay exposure was found to be 0.80 lux.sec.

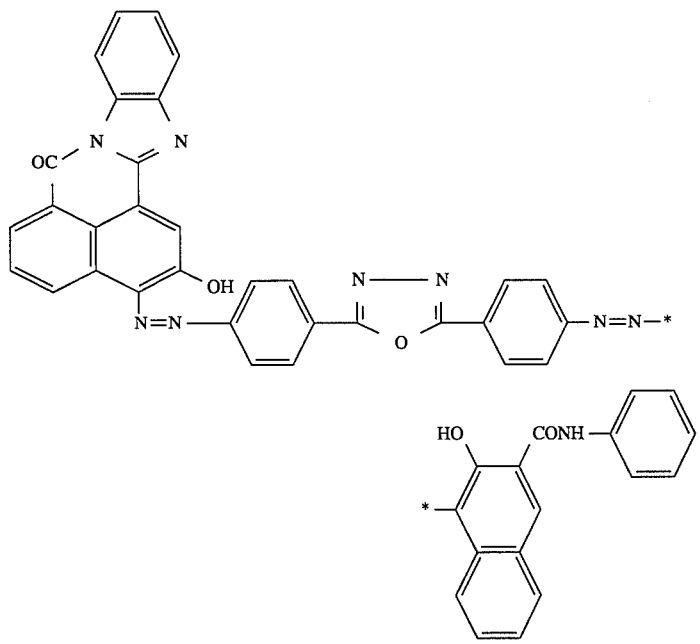

Example 4

An electrophotographic photoreceptor was fabricated in a similar manner as Example 1, except that the titanium oxyphthalocyanine pigment used in Example 1 was replaced by naphthal bis-azo pigment represented by the formula below. Thus obtained electro-photographic photoreceptor was tested for sensitibity by exposing it to white light and the half decay exposure was found to be 0.97 lux.sec.

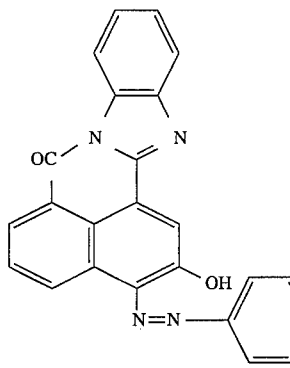

Examples 5 to 12

In each of these examples, an electrophotographic photoreceptor was fabricated in a similar manner as Example 1, except that the arylamine hydrazone compound used in Example 1 was replaced by anyone of arylamine hydrazone compounds shown in the Table 1 below prepared in a similar way to the Preparation 1 or 2.

TABLE 1

| Examples | Compound No. | sensitivity ($\mu J/cm^2$) |
| --- | --- | --- |
| 5 | 2 | 0.51 |
| 6 | 4 | 0.46 |
| 7 | 6 | 0.50 |
| 8 | 9 | 0.53 |
| 9 | 13 | 0.52 |
| 10 | 15 | 0.50 |
| 11 | 17 | 0.55 |
| 12 | 22 | 0.54 |

Examples 13 to 20

In each of these examples, an electrophotographic photoreceptor was fabricated in a similar manner as Example 3, except that the arylamine hydrazone compound used in Example 3 was replaced by anyone of arylamine hydrazone compounds shown in the Table 2 below prepared in a similar way to the Preparation 1 or 2.

TABLE 2

| Examples | Compound No. | sensitivity (lux.sec) |
| --- | --- | --- |
| 13 | 2 | 0.82 |
| 14 | 4 | 0.77 |
| 15 | 6 | 0.80 |
| 16 | 9 | 0.85 |
| 17 | 13 | 0.87 |
| 18 | 15 | 0.74 |
| 19 | 17 | 0.88 |
| 20 | 22 | 0.85 |

Comparative example 1

An electrophotographic photoreceptor was fabricated in a similar manner as Example 1, except that the arylamine hydrazone compound used in Example 1 was replaced by the comparative compound 1 shown below.

Comparative compound 1:

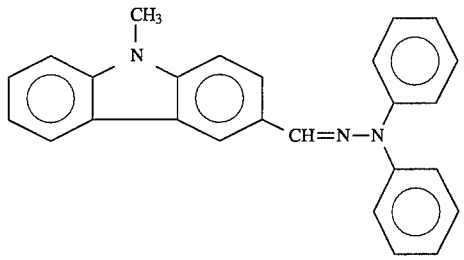

Then, the obtained electrophotographic photoreceptor was tested for sensitivity and residual potential in a similar way as Example 1. The results are shown in the Table 3 together with those of Example 1.

Comparative example 2

An electrophotographic photoreceptor was fabricated in a similar manner as Comparative example 1, except that the comparative compound 1 of Comparative example 1 was replaced by the comparative compound 2 shown below. Then, the obtained electrophotographic photoreceptor was tested for sensitivity and residual potential. The results are shown in the Table 3 below.

Comparative compound 2:

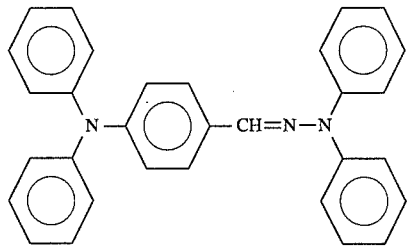

TABLE 3

| Example | sensitivity ($\mu J/cm^2$) | residual potential (V) |
| --- | --- | --- |
| Comp. ex. 1 | 0.60 | −27 |
| Comp. ex. 2 | 0.59 | −12 |
| Example 1 | 0.49 | −5 |

It is obvious from the Table 3 that the compound of Example 1 exhibits better values both in sensitivity and in residual potential as compared to the compounds of Comparative examples 1 and 2.

Example 21

An electrophotographic photoreceptor was fabricated in a similar manner as Example 1, except that the arylamine hydrazone compound used in Example 1 was replaced by the arylamine hydrazone compound prepared in Preparation 3 (Compound No. 28).

Thus obtained electrophotographic photoreceptor provided with a two-layered photosensitive layer was tested for sensitivity as described in Example 1 and the sensitivity was found as a half decay exposure of 0.49 μJ/cm². The residual potential represented by the surface potential at exposure time of 9.9 seconds was found to be −4V. After repeated 2000 cycles of the aforementioned processes, it was not observed any rise of the residual potential. When the surface voltage obtained by negatively charging at 50 μA corona current in the dark was denoted by $V_0$ and the surface voltage obtained by irradiating with 3000 lux white light for 5 minutes and then negatively charging in a similar manner was denoted by V, the retention percentage at intense exposure expressed by $(V/V_0) \times 100(\%)$ was 92.1 %.

When the surface potential obtained by negatively charging after repeated 100 cycles of negative charging-exposure process was denoted by V', the restoration percentage at intense exposure expressed by $(V'/V_0) \times 100(\%)$ was 93.5%.

Example 22

An electrophotographic photoreceptor was fabricated in a similar manner as Example 21, except that the titanium oxyphthalocyanine pigment used in Example 21 was replaced by the titanium oxyphthalocyanine pigment exhibiting strong diffraction peaks at Bragg angles$(2\theta \pm 0.2°)$ 9.5°, 27.1° and 27.3°. Thus obtained electrophotographic photoreceptor was tested for sensitivity by exposing it to light at 780 nm and the half decay exposure was found to be 0.12 μJ/cm². The residual potential was found to be −5V, the retention percentage at intense exposure was 91.3% and the restoration percentage at intense exposure was 92.8%.

Example 23

An electrophotographic photoreceptor was fabricated in a similar manner as Example 21, except that the phthalocyanine pigment used in Example 21 was replaced by the naphthal bis-azo pigment used in Example 3. Thus obtained electrophotographic photoreceptor was tested for sensitivity by exposing it to white light and the half decay exposure was found to be 0.78 lux.sec. The residual potential was found to be −5V, the retention percentage at intense exposure was 90.5% and the restoration percentage at intense exposure was 91.6%.

Example 24

An electrophotographic photoreceptor was fabricated in a similar manner as Example 21, except that the phthalocyanine pigment used in Example 21 was replaced by the naphthal bis-azo pigment used in Example 4. Thus obtained electrophotographic photoreceptor was tested for sensitivity by exposing it to white light and the half decay exposure was found to be 0.99 lux.sec. The residual potential was found to be −8V, the retention percentage at intense exposure was 90.3% and the restoration percentage at intense exposure was 92.0%.

Examples 25 to 32

In each of these examples, an electrophotographic photoreceptor was fabricated in a similar manner as Example 21, except that the arylamine hydrazone compound used in Example 21 was replaced by an arylamine hydrazone compound shown in the Table 4 prepared in a similar manner as Preparations 3 to 6. The obtained electrophotographic photoreceptors were tested for sensitivity, residual potential and retention percentage at intense exposure and the results are shown in the Table 4.

TABLE 4

| Ex. | Comp. No. | sensitivity (μJ/cm²) | residual potential (V) | retention percent at intense expo. (%) |
|---|---|---|---|---|
| 5 | 36 | 0.50 | −5 | 91.8 |
| 6 | 38 | 0.49 | −4 | 90.3 |
| 7 | 42 | 0.56 | −10 | 92.1 |
| 8 | 46 | 0.58 | −9 | 91.5 |
| 9 | 53 | 0.47 | −3 | 91.1 |
| 10 | 54 | 0.48 | −5 | 92.0 |
| 11 | 63 | 0.51 | −7 | 91.7 |
| 12 | 67 | 0.45 | −2 | 92.2 |

Examples 33 to 40

In each of these examples, an electrophotographic photoreceptor was fabricated in a similar manner as Example 23, except that the arylamine hydrazone compound used in Example 23 was replaced by an arylamine hydrazone compound shown in the Table 5 prepared in a similar manner as Preparations 3 to 6. The obtained electrophotographic photoreceptors were tested for sensitivity, residual potential and retention percentage at intense exposure and the results are shown in the Table 5.

TABLE 5

| Ex. | Comp. No. | sensitivity (lux.sec) | residual potential (V) | retention percent at intense expo. (%) |
|---|---|---|---|---|
| 13 | 36 | 0.81 | −6 | 91.0 |
| 14 | 38 | 0.79 | −5 | 90.8 |
| 15 | 42 | 0.90 | −11 | 93.0 |
| 16 | 46 | 0.95 | −10 | 92.4 |
| 17 | 53 | 0.83 | −4 | 90.7 |
| 18 | 54 | 0.82 | −5 | 91.9 |
| 19 | 63 | 0.85 | −12 | 90.5 |
| 20 | 67 | 0.76 | −4 | 91.4 |

Comparative example 3

An electrophotographic photoreceptor was fabricated in a similar manner as Example 21, except that the arylamine hydrazone compound used in Example 21 was replaced by Comparative compound 1 used in Comparative example 1.

Then, the obtained electrophotographic photoreceptor was tested for sensitivity, residual potential and retention percentage at intense exposure in a similar manner as Example 21. The results are shown in the Table 6 together with the results of the electrophotographic photoreceptor of Example 21.

Comparative example 4

An electrophotographic photoreceptor was fabricated in a similar manner as Comparative example 3, except that Comparative compound 1 used in Comparative example 3 was replaced by Comparative compound 2 used in the Comparative example 2. The obtained electrophotographic photoreceptor was tested for sensitivity, residual potential and retention percentage at intense exposure. The results are shown in the Table 6.

Comparative example 5

An electrophotographic photoreceptor was fabricated in a similar manner as Comparative example 3, except that Comparative compound 1 used in Comparative example 3 was replaced by Comparative compound 3 set forth below. The obtained electrophotographic photoreceptor was tested for sensitivity, residual potential and retention percentage at intense exposure. The results are shown in the Table 6.

Comparative compound 3:

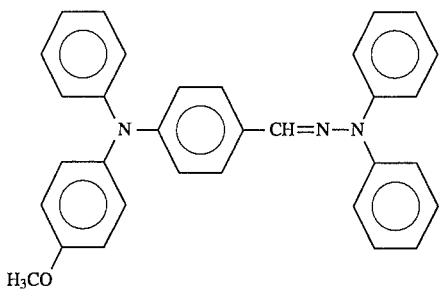

TABLE 6

| Example | sensitivity ($\mu J/cm^2$) | residual potential (V) | retention percent at intense expo. (%) |
|---|---|---|---|
| Comp. ex. 3 | 0.60 | −27 | 85.9 |
| Comp. ex. 4 | 0.59 | −12 | 90.0 |
| Comp. ex. 5 | 0.59 | −11 | 81.3 |
| Example 21 | 0.49 | −4 | 92.1 |

It is obvious from the Table 6 that the compound of Example 21 was, as compared to the compounds of Comparative examples 3 to 5, superior in sensitivity, residual potential and retention percentage at intense exposure.

What is claimed is:

1. An electrophotographic photoreceptor comprising on a conductive support a photosensitive layer containing an arylamine hydrazone compound represented by the general formula (I):

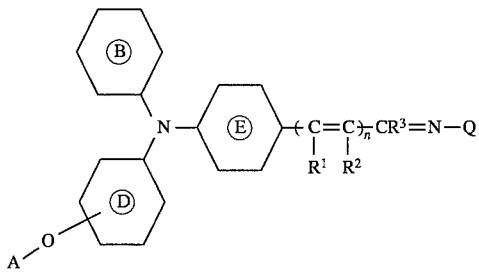

[I]

in which,

A represents a group of the general formula (II), (III) or (IV):

$$-X-Ar \quad \text{[II]}$$

[III]

[IV]

Q represents a group of the general formula (V):

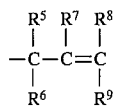

[V]

n is 0 or an integer equal to or more than 1;

X represents an optionally substituted alkylene group;

Ar represents an optionally substituted aryl group or an optionally substituted heterocyclic group;

B, D and E each represents a benzene ring optionally substituted with at least one substituent;

$R^1$, $R^2$, $R^3$, $R^5$, $R^6$, $R^7$, $R^8$ and $R^9$ each represents a hydrogen atom, an optionally substituted alkyl group, an optionally substituted aryl group or an optionally substituted heterocyclic group, provided that when n is equal to or more than 2, each $R^1$ in each structural unit may be identical or different each other and the same is true case of $R^2$;

$R^4$ represents an optionally substituted alkyl group, an optionally substituted aryl group, an optionally substituted heterocyclic group or an optionally substituted aralkyl group;

$R^{10}$ and $R^{11}$ each represents an optionally substituted aryl group, an optionally substituted heterocyclic group, an optionally substituted alkyl group, an optionally substituted aralkyl group or allyl group, provided that $R^{10}$ and $R^{11}$ may be bonded directly or by means of a linking group.

2. The electrophotographic photoreceptor according to claim 1, wherein the compound of the general formula (I) is represented by the general formula (I'):

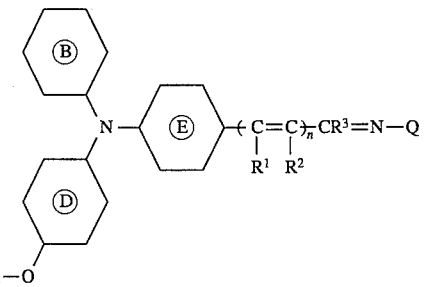

[I']

3. The electrophotographic photoreceptor according to claim 1 or 2, wherein the compound of the general formula (I) is represented by the general formula (I"):

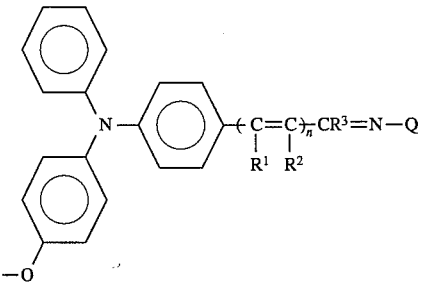

[I"]

4. The electrophotographic photoreceptor according to anyone of claims 1 to 3, wherein the substituent A in the general formula (I) is represented by the general formula (II).

5. The electrophotographic photoreceptor according to anyone of claims 1 to 3, wherein the substituent A in the general formula (I) is represented by the general formula (IV).

6. The electrophotographic photoreceptor according to anyone of claims 1 to 3, wherein the substituent A in the general formula (I) is represented by the general formula (III).

7. The electrophotographic photoreceptor according to anyone of claims 1 to 3, wherein the substituent Q in the general formula (I) is represented by the structural formula:

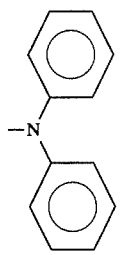

8. The electrophotographic photoreceptor according to anyone of claim 1 to 3, wherein the number n in the general formula (I) is 0, 1 or 2.

9. The electrophotographic photoreceptor according to claim 1, characterized in that a photosensitive layer thereof consists of a charge generate layer and at least a charge transport layer, said arylamine hydrazone compound of the general formula (I) being contained in said charge transport layer.

10. The electrophotographic photoreceptor according to claim 9, characterized in that said charge transport layer contains a binder.

11. The electrophotographic photoreceptor according to claim 9, characterized in that said charge generation layer contains a metal-free phthalocyanine or a metallic phthalocyanine.

* * * * *